(12) United States Patent
Frecker et al.

(10) Patent No.: US 7,208,005 B2
(45) Date of Patent: Apr. 24, 2007

(54) MULTIFUNCTIONAL TOOL AND METHOD FOR MINIMALLY INVASIVE SURGERY

(75) Inventors: Mary I. Frecker, State College, PA (US); Randy S. Haluck, Hershey, PA (US); Ryan P. Dziedzic, McLean, VA (US); Jeremy R. Schadler, Fleetwood, PA (US)

(73) Assignee: The Penn State Research Foundation, University Park, PA (US)

( * ) Notice: Subject to any disclaimer, the term of this patent is extended or adjusted under 35 U.S.C. 154(b) by 482 days.

(21) Appl. No.: 10/213,645

(22) Filed: Aug. 5, 2002

(65) Prior Publication Data

US 2003/0065358 A1    Apr. 3, 2003

Related U.S. Application Data

(60) Provisional application No. 60/310,315, filed on Aug. 6, 2001, provisional application No. 60/310,314, filed on Aug. 6, 2001.

(51) Int. Cl.
*A61B 17/295*  (2006.01)
*A61B 17/32*  (2006.01)

(52) U.S. Cl. ................................ 606/205; 606/167
(58) Field of Classification Search .................. None
See application file for complete search history.

(56) References Cited

U.S. PATENT DOCUMENTS

| | | | | |
|---|---|---|---|---|
| 5,334,198 A * | 8/1994 | Hart et al. | ...................... | 606/52 |
| 5,456,684 A * | 10/1995 | Schmidt et al. | ................ | 606/41 |
| 5,542,949 A | 8/1996 | Yoon | | |
| 5,665,100 A * | 9/1997 | Yoon | ........................... | 606/170 |
| 5,808,665 A | 9/1998 | Green | | |
| 5,928,255 A | 7/1999 | Meade et al. | | |
| 5,984,938 A | 11/1999 | Yoon | | |
| 6,126,665 A | 10/2000 | Yoon | | |
| 6,187,026 B1 | 2/2001 | Devlin et al. | | |
| 6,206,903 B1 * | 3/2001 | Ramans | ...................... | 606/205 |
| 6,377,011 B1 | 4/2002 | Ben-Ur | | |
| 6,773,444 B2 * | 8/2004 | Messerly | .................... | 606/169 |
| 2003/0208186 A1 * | 11/2003 | Moreyra | ........................ | 606/1 |

FOREIGN PATENT DOCUMENTS

WO    WO 99/29238    6/1999
WO    WO 00/33723    6/2000

OTHER PUBLICATIONS

Marcus Rebel, Jun. 30, 1994, DE 43 38 510 A1.
Canfield, Edinger, Frecker, Koopman, Design of Piezoelectric Inchworm Actuator and Complaint End-Effector for Minimally Invasive Surgery, SPIE's 6th International Symposium, Mar. 1999.
Endoscopic Instruments—conventional and intelligent.

* cited by examiner

*Primary Examiner*—Glenn K. Dawson
(74) *Attorney, Agent, or Firm*—McKee, Voorhees & Sease, P.L.C.

(57) ABSTRACT

An apparatus and method for minimally invasive surgery. The apparatus can comprise a tool which includes a multifunctioning end effector for insertion into a patient, a user control adapted for use by the surgeon external of the patient, and an intermediate section between the end effector and the user control to translate control instructions from the user control through an actuating mechanism to operate the end effector in one of at least two different functioning states. No instrument exchange is necessary to change between states. The actuation mechanism could be a manually operated mechanical mechanism. Alternatively, it could be partially or fully electromechanical or electrical or electronic. According to one aspect, the end effector is a rigid link mechanism. According to another aspect, the end effector could be a compliant mechanism, at least in part. Another aspect of the invention includes the ability of the end effector to have at least some articulation in addition to grasping and cutting functions.

22 Claims, 30 Drawing Sheets

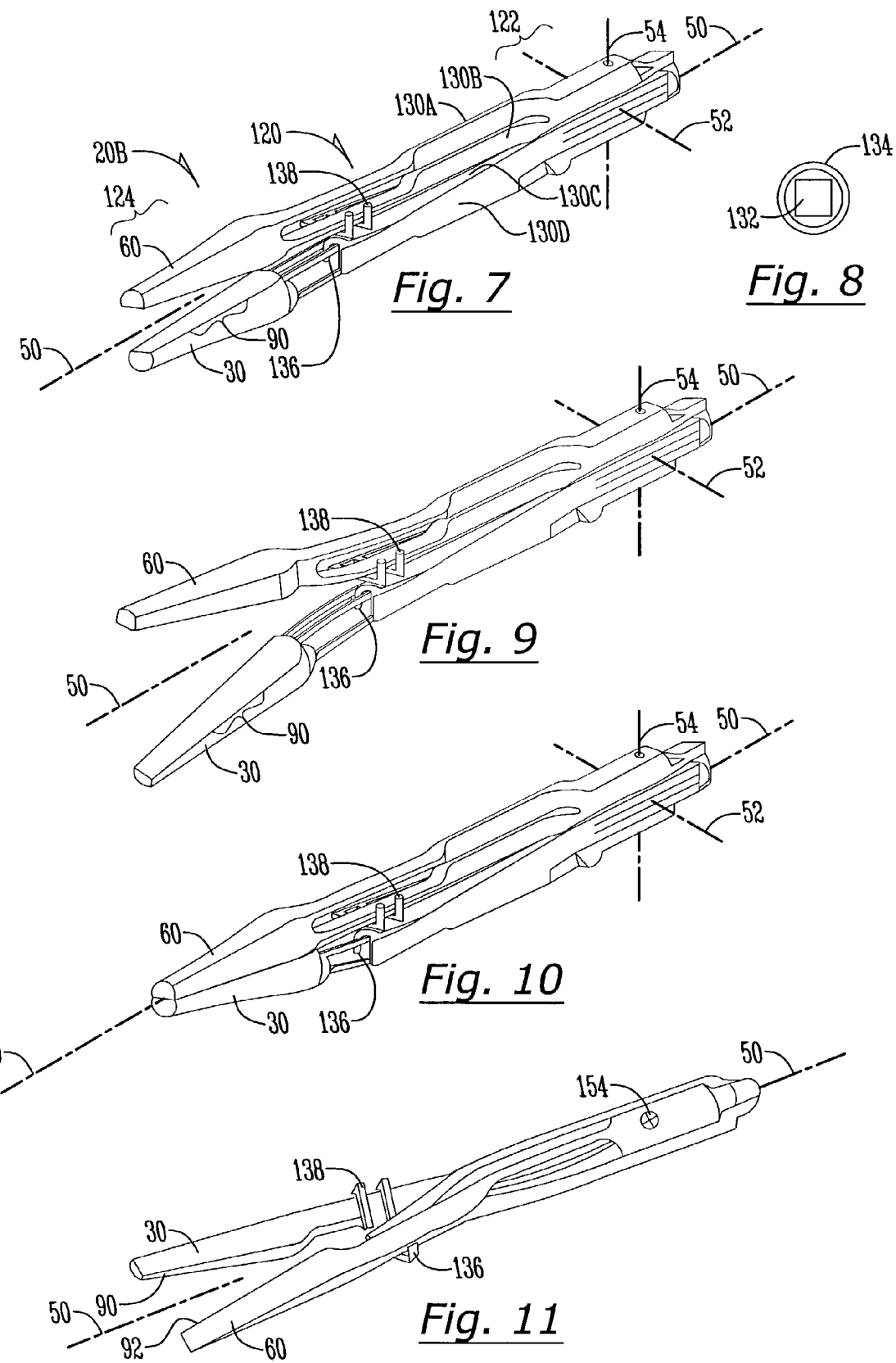

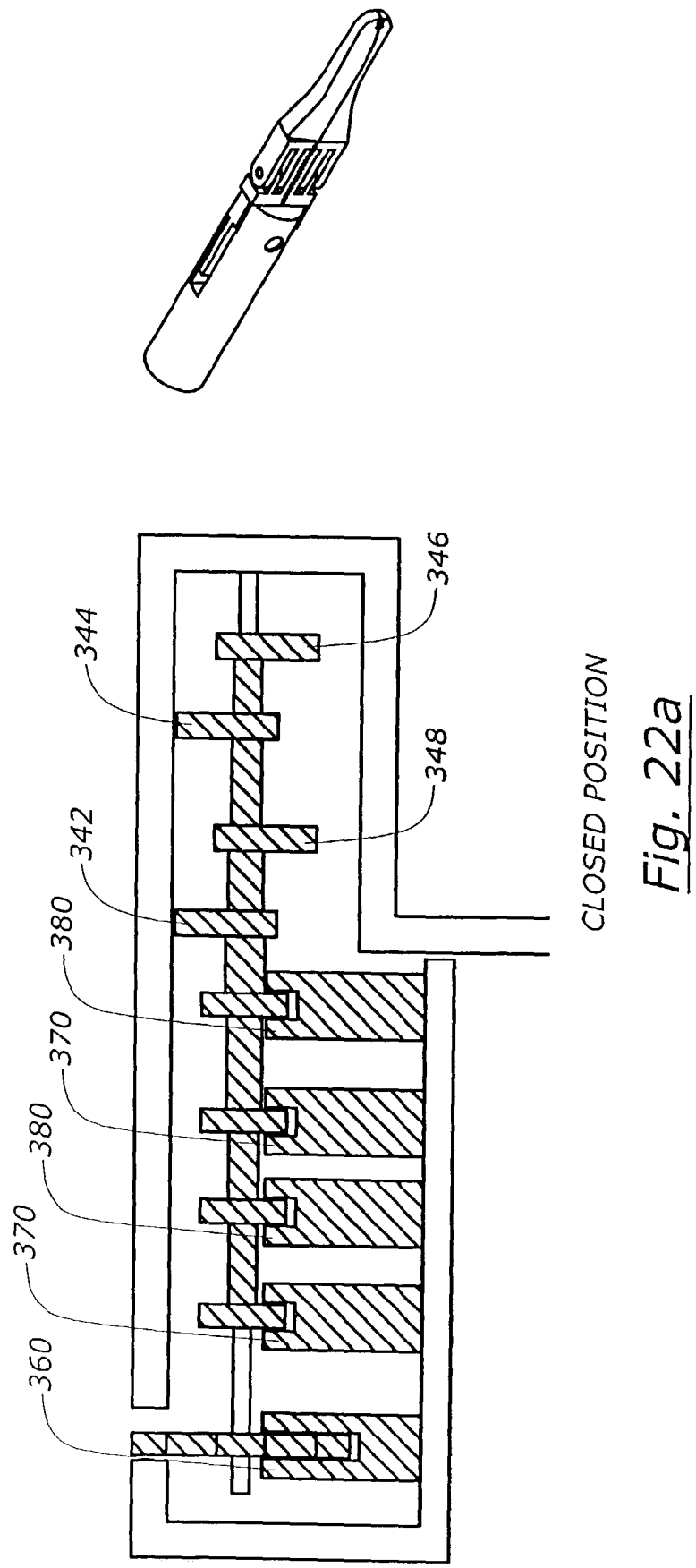
Fig. 22a  CLOSED POSITION

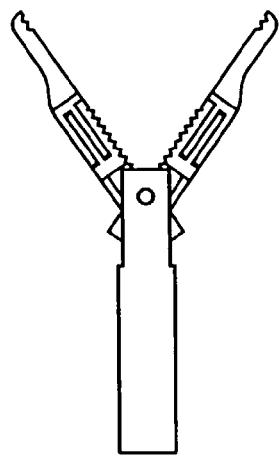
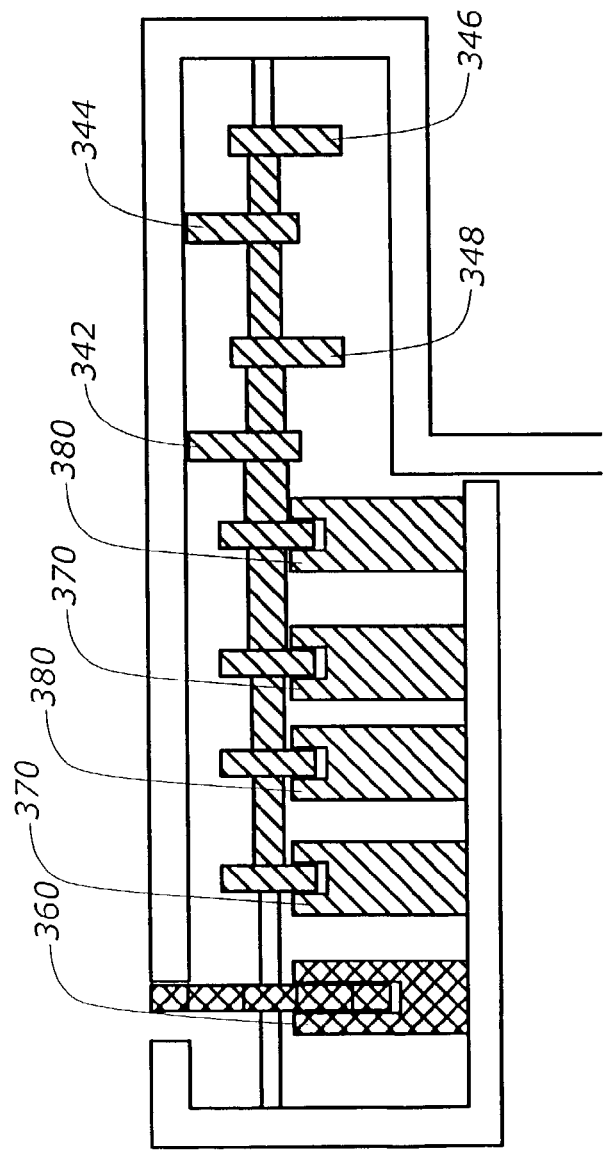
OPEN GRASPING POSITION
*Fig. 22b*

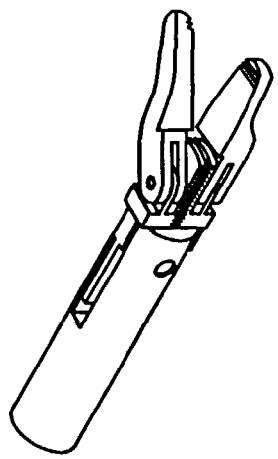
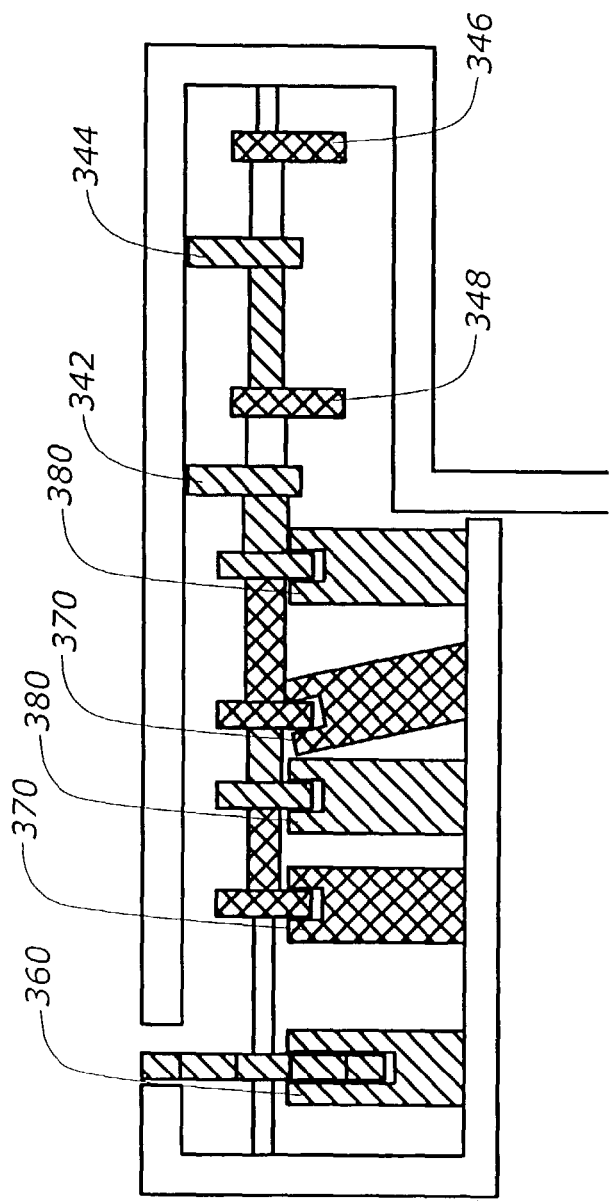
*Fig. 22c*
OPEN CUTTING POSITION

CLOSED ARTICULATED GRASPING POSITION

OPEN ARTICULATION POSITION

MULTIFUNCTIONAL TOOL AND METHOD FOR MINIMALLY INVASIVE SURGERY

REFERENCE TO RELATED APPLICATIONS

This application is based upon U.S. Provisional Application Ser. No. 60/310,314, filed Aug. 6, 2001, and Ser. No. 60/310,315, filed Aug. 6, 2001.

INCORPORATION BY REFERENCE

The entire contents of U.S. Provisional Applications Ser. Nos. 60/310,314, and 60/310,315,both filed Aug. 6, 2001, are incorporated by reference herein.

I. BACKGROUND OF THE INVENTION

A. Field of the Invention

This invention relates to Minimally Invasive Surgery tools and methods, and in particular, to multifunction tools and methods.

B. Problems in the Art

Recent advances in the medical sciences have lead to the continued acceptance of Minimally Invasive Surgery ("MIS"). Originally envisioned as far back as about 1900, MIS is today being considered as a replacement to traditional "open" surgeries throughout the body including the chest, spine, abdomen, and pelvis. The major difference between MIS and traditional surgery is the surgeon's access to the patient. During MIS, the surgeon makes several small incisions (under one centimeter) in the patient's skin to gain access to the patient's body. Through one of these incisions is placed the endoscope—a narrow cylindrical scope attached to a camera. The remaining ports allow a variety of specially designed surgical instruments to enter the operating area.

MIS offers many significant advantages to conventional surgery. Traditionally, most postoperative problems have been a result of the large wounds left from open surgery. This leads to long hospital stays, lengthy aberration from normal life, high health care costs, and great personal pain and discomfort. MIS has the potential to reduce recovery time from weeks to days. Furthermore, MIS reduces bowel handling and serosal drying—the two major causes of recovery irritation (Cuschieri, Alfred, 1992. Laparoscopic Biliary Surgery. Oxford: Blackwell Scientific, 1992, pp. 26–98.)

While MIS offers many potential benefits to the patient, there are a number of obstacles standing in the way of more widespread use. First, the surgeon cannot view the operating area in three dimensions. This is a result of the endoscope's image being displayed on a television monitor. Second, the perception of distances within the body is a function of their orientation with respect to the endoscope. Objects that are closer to the endoscope will appear much larger than objects that are further away (Cuschieri, 1992. Id.). Finally, the surgical instruments themselves continue to be a limiting factor in the advancement of MIS because of limited mobility and lack of multifunctionality. While the first two of these obstacles can be overcome with practice and proficiency on the surgeon's part, the third suggests the need for the development of new and innovative tools for MIS.

There is a need in the art for more versatile tools for MIS that have the potential to expand the capability of MIS surgical instruments currently commercially available. To meet this goal, a number of current limitations have been identified.

First, most conventional tools possess only four degrees of freedom. These include translation along the longitudinal axis of the instrument, rotation around the longitudinal axis of the instrument, relative rotation around the entry point of the instrument to the body, and the opening and closing of the gripper's jaws (Melzer, A Q., G. Buess, and A. Cuschieri, 1992. Operative Manual of Endoscopic Surgery. Berlin: Springer Varlag, 1992, pp. 14–36.) Due to the kinetic qualities of the human hand and arm, during open surgery the surgeon can perform movements of approximately twenty degrees of freedom (Melzer, 1996. "Endoscopic Instruments—Conventional and Intelligent.", Endosurgery, New York: Churchill Livingstone, 1996, pp. 69–95.) Because the conventional surgeon's motion is virtually unimpeded by external constraints, the minimally invasive surgeon looses a significant amount of control due to limited degrees of freedom.

Second, there is a need for multifunctional MIS tools. Multifunctional tools could provide several advantages over standard single function tools. Studies have shown that 10–30% of total operating time is used for changing between tools with single functions (Metzler 1996,Id.). Multifunctional tools have the potential to reduce tool changeover time by having the ability to perform two or more previously distinct functions in one. Besides increasing operative time, tool changeover can lead to uncontrollable bleeding. During a tool switch the tissue being worked on needs to be subsequently grasped, coagulated and transected before a new tool can be inserted. Bleeding may occur at any point during this process immediately impeding the view of the surgeon (Melzer 1996,Id.). Studies have shown that the primary reason for converting from a minimally invasive technique to open surgery is uncontrollable bleeding (Cuschieri, A., F. Dubois, J. Mouiel, P. Mouret, H. Becker, G, Buess, M. Trede, H. Troild, 1991. "The European Experience with Laparscopic Cholecystectomy." American Journal of Surgery, Vol. 161, pp. 385–387.) Exchange time, disruption of process flow for the surgical procedure, risk of tissue injury, and other issues regarding tool utilization in MIS are discussed in more detail at Mehta, N., Haluck R., Frecker M., Snyder, A. (2002) Sequence and Task Analysis of Instrument Use in Common Laprascopic Procedures. Surgical Endoscopy, 16, 280–285.

Third, minimally invasive surgical tools are only mobile around the fixed access point of entry into the operating area. Once an initial insertion is made into a patient, a fixed trocar sleeve is put in place through which tools can then be slid in and out. The trocar sleeve defines a conical section in the operative cavity that will be accessible with the surgical instrument. The limitations of this conical section require significant manual dexterity on the part of the operating surgeon (Cuschieri, 1992, supra).

Fourth, conventional tools lack the ability to reach behind obstructions. There are a number of instances during surgery that the surgeon needs to access a point behind a vessel or tissue. Presently available tools make this motion impossible and require the surgeon to find a different, less optimal, line of approach.

There are a number of issues that must be dealt with when developing a new minimally invasive tool. The first of these issues is reposability. A reposable instrument is one that can be re-used. If an instrument is to be reposable then it must have the ability to be completely sterilized. In order to be sterilized, the instrument must have the ability to withstand autoclave temperature of 15 to 120° C. or gas sterilization temperature of 127° F. with 100% humidity (Cappelleri, D., M. Frecker, T. Simpson, and A. Snyder. 1999. "A Metamodel-Based Approach for Optimal Design of a PZT Bimorph Actuator for Minimally Invasive Surgery." ASME Journal of Mechanical Design, 24, 2, pp. 354–357.) Alternatives to reposable instruments are disposable instruments. Disposable instruments greatly reduce preparation time by eliminating the need for sterilization. However, using disposable instruments is approximately ten times most costly than using reposable instruments. Furthermore, disposable instruments tend to be less precise than reposable ones and raise ecological concerns (Melzer, 1996,Id.).

Another issue is the ergonomics of the instrument. It has been suggested that an MIS instrument handle has to function independently of the rotation of the instrument tip. Expanding this axiom to a multi-degree of freedom design, preferably all degrees of freedom must function independently of one and other. Additionally, all functions of the instrument preferably must be capable of being carried out with one hand.

There are a number of present design preferences for a MIS grasping tool including but not limited to opening width of jaws, length of jaws, t response time of jaws, and force required to clamp a suture needle.

The maximum diameter of the tool is limited by the inner diameter of the trocar sleeve being used in surgery. Presently trocar sleeve inner diameters of twelve, nine, seven, five, and three millimeters are in common use. The trend in MIS is towards instruments of smaller and smaller diameters. This trend places more emphasis on the development of instruments at the smallest end of the available spectrum.

Therefore, a need in the art has been identified, namely the need for a new tool for MIS that responds to the current limitations and the general requirements of minimally invasive instruments.

There have been several attempts at creating a multi-degree of freedom gripper prior to this paper. An example of a commercially available multi-degree of freedom gripper is called the Roticulator™ available from USSC, Norwalk, Conn., USA. The Roticulator achieves its fifth degree of freedom with the addition of a semi-rigid link between the handle and the jaws of the instrument. As the link is extended beyond the confinement of the handle, the stresses causes by the handle are released allowing the link to return to its naturally curved shape. When the link is fully extended, the gripper is at approximately a 63.5-degree angle with the centerline of the instrument. One issue is the Roticulator's inability to resist a force perpendicular to its jaws when extended. To combat this problem, surgeons have taken to placing a clamp on the instrument such that the tool cannot rotate along the long axis of the instrument. This allows the tool to resist a perpendicular force however it also eliminates a degree of freedom from the instrument. This returns the tool's capabilities to the standard three degrees of freedom.

Furthermore, as the instrument is rotated around its long axis, the tip sweeps out a circle. This is substantially different from the traditional gripper who exhibits simple rotation about its axis during the same action. As a result, the axial orientation of the tip cannot be changed in the extended position without considerable experience on the part of the surgeon (Melzer, 1996, supra.).

A. Melzer et. al. have proposed meeting the need for instruments with increased degrees of freedom by introducing a controllable ball-and-socket joint into the shaft of a gripper (Melzer, 1992, supra.). Every movement of the handle at the outer joint would be translated to a similar movement of the inner ball-and-socket. Such an instrument would be based on the mechanical remote-control grasper currently used in advanced industrial applications (Melzer, 1992,Id.). Presently, it is not believed that such a design has advanced beyond the conceptual phase for use in MIS.

In order to allow a gripper's tip to both pivot and rotate, the axis of pivot preferably should lie along the centerline of the instrument. A need has been identified in the art to achieve this criterion.

II. SUMMARY OF THE INVENTION

A. Brief Summary of the Invention

The present invention includes apparatus and methods for MIS. One apparatus comprises a tool which includes a multi-functioning end effector for insertion into a patient, a user control adapted for use by the surgeon externally of the patient, and an intermediate section between the end effector and the user control to translate control instructions from the user control through an actuating mechanism to operate the end effector in one of at least two different functioning states. No instrument exchange is necessary to change between states. The actuation mechanism could be a manually operated mechanical mechanism. Alternatively, it could be partially or fully electromechanical or electrical or electronic. According to one aspect, the end effector is a rigid link mechanism. According to another aspect, the end effector could be a compliant mechanism, at least in part. Another aspect of the invention includes the ability of the end effector to have at least some articulation in addition to other functions.

In one aspect of an apparatus according to the invention, the end effector includes first and second jaws. The jaws include surfaces that can effectuate grasping or dissecting, or surfaces that can effectuate cutting by scissors action. Compliant or non-compliant structure between the jaws and actuating mechanism facilitates translation of actuation movement to movement of cutting edges or blades on jaws in a scissors action. Another aspect utilizes compliant structure to enable not only movement of jaws relative to one another in a first plane, but conversion between operation of the tool in such a first state, where the jaws move towards and away from each other in response to a first actuation or input force, but also operation in a second mode or state where jaws move towards and away from each other in response to a second actuation or input force. In one aspect, the device automatically switches from state to state dependent on the input force or the selection of actuation. In one aspect, the device automatically switches from state to state dependent on the input force or the selection of actuation.

In a further aspect of an apparatus according to the invention, each jaw is along a longitudinal axis between a proximal end and a distal end, and has a grasping surface along at least a portion of it. A cutting surface or blade is formed in or positioned on or in the margin of one side of the grasping surface of each jaw. In one embodiment, when the grasping surfaces of the jaws are brought together, the cutting blades are on opposite sides for each jaw, but near or in the same plane as the grasping surface of its jaw. When in the first state, the jaws are aligned with the grasping surface of each jaw facing each other and the jaws are moveable generally in a first plane relative to one another between a closed position, where grasping surfaces of the jaws come in close proximity, or into abutment at least at some points, and an open position where there is separation between grasping surfaces. Actuation pivots the jaws between open and closed positions in the first functional state for the tool. When in the second functional state, the blades of the jaws are aligned and moveable by actuation generally in a second plane relative to one another between a closed position, where cutting blades come into close proximity or overlap one another, and an open position where there is separation between cutting blades. Actuation pivots the cutting blades, generally in the second plane in a scissors action between open and closed positions. Actuation forces can be translated to the blades by compliant or non-compliant mechanism(s), or combinations thereof.

In one aspect of the invention, at least one jaw has a distal section that is mechanically linked to a proximal section. The distal section can move in the second plane when the tool is in the second functional state (the cutting state), but moves in the first plane in the first functional state (the grasping state).

In another aspect of the invention, both jaws have distal sections that are mechanically linked to their respective proximal sections. The distal sections can move in the second plane when the tool is in the second functional state, but move in a first plane in the first functional state.

In a still further aspect of the invention, if both jaws have mechanically linked distal sections, those sections can be articulated in the second plane. The articulation can either be in the same direction; to create articulated grasping jaws to either side of the first plane. When the jaws are moved in the first plane, the articulated distal sections function as articulated grasping or dissecting jaws. If the articulation of the distal sections is in opposite directions and the jaws are in a closed position, the distal sections can be moved relative to one another to create two moving scissors blades.

In a method according to one aspect of the invention, multiple functions from an end effector can be performed without tool exchange by actuating jaws inside the patient to bring grasping surfaces towards and away from one another in a fist functional state, and actuating the jaws so that at least portions of the jaws having cutting surfaces can be brought towards and away from one another in a second functional state. In a further aspect of a method according to the invention, the movement of the jaws in first and second states could be by mechanical linkage or by compliant mechanism. In another aspect, articulation of a section of the jaws adds another function to the end effector.

B. Objects, Features, or Advantages of the Invention

Multi-functionality in minimally invasive surgery tools and methods is expected to benefit both surgeons and patients by decreasing the number of tool exchanges required, shortening operation time, reducing risk of inadvertent tissue trauma during instrument exchanges, and minimizing disruption of the surgeon's train of thought during a procedure. Having a multifunctional instrument may result in improved surgical techniques since the surgeon will be less likely to use a single function tool for purposes other then its intended purpose. The articulating feature will also add to the versatility of the instrument allowing the surgeon to have non-linear access, which is currently unavailable from existing single function tools.

It is therefore a principle aspect, object, feature, or advantage of the present invention to provide an apparatus and method for MIS, which improves over and/or solves problems and deficiencies in the state of the art.

Further aspects, objects, features, or advantages of the present invention include an apparatus and method for MIS which:

(a) is flexible and versatile, including the capability of multifunction and substantial degree of freedom of movement.

(b) Easily, efficiently, and effectively changes between functions;

(c) Does not substantially increase size or cost of the apparatus, and may be amenable to miniaturization or automation;

(d) Reduces time needed for operative procedures;

(e) Reduces disruption of the process flow of the operation;

(f) Reduces risk of injury during operations;

(g) May be implemented in resposibles and disposibles;

(h) Retains most or all needed functional requirements of MIS;

(i) Is durable;

(j) Is economical;

(k) Increases the effectiveness of the surgeon and the surgery.

These and other aspects, objects, features, or advantages of the invention will become more apparent with reference to the accompanying specification and claims.

III. BRIEF DESCRIPTION OF THE DRAWINGS

Figure 2:
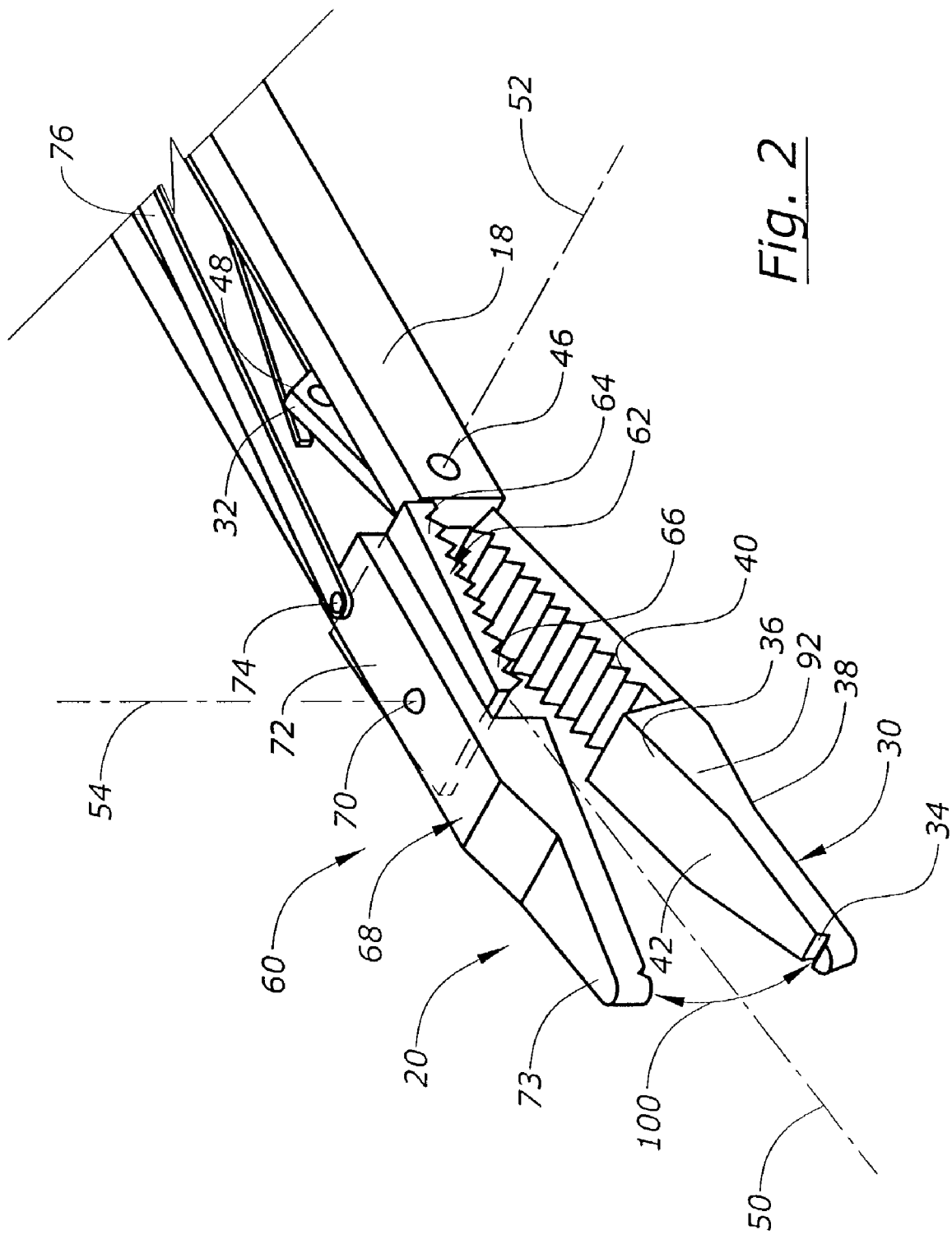
FIG. 2 is an enlarged perspective view of an end effector according to an embodiment of the present invention that could be used with the tool of FIG. 1 showing, for generally a side view, the end effector in a first or grasping state (jaws open).
Figure 3:
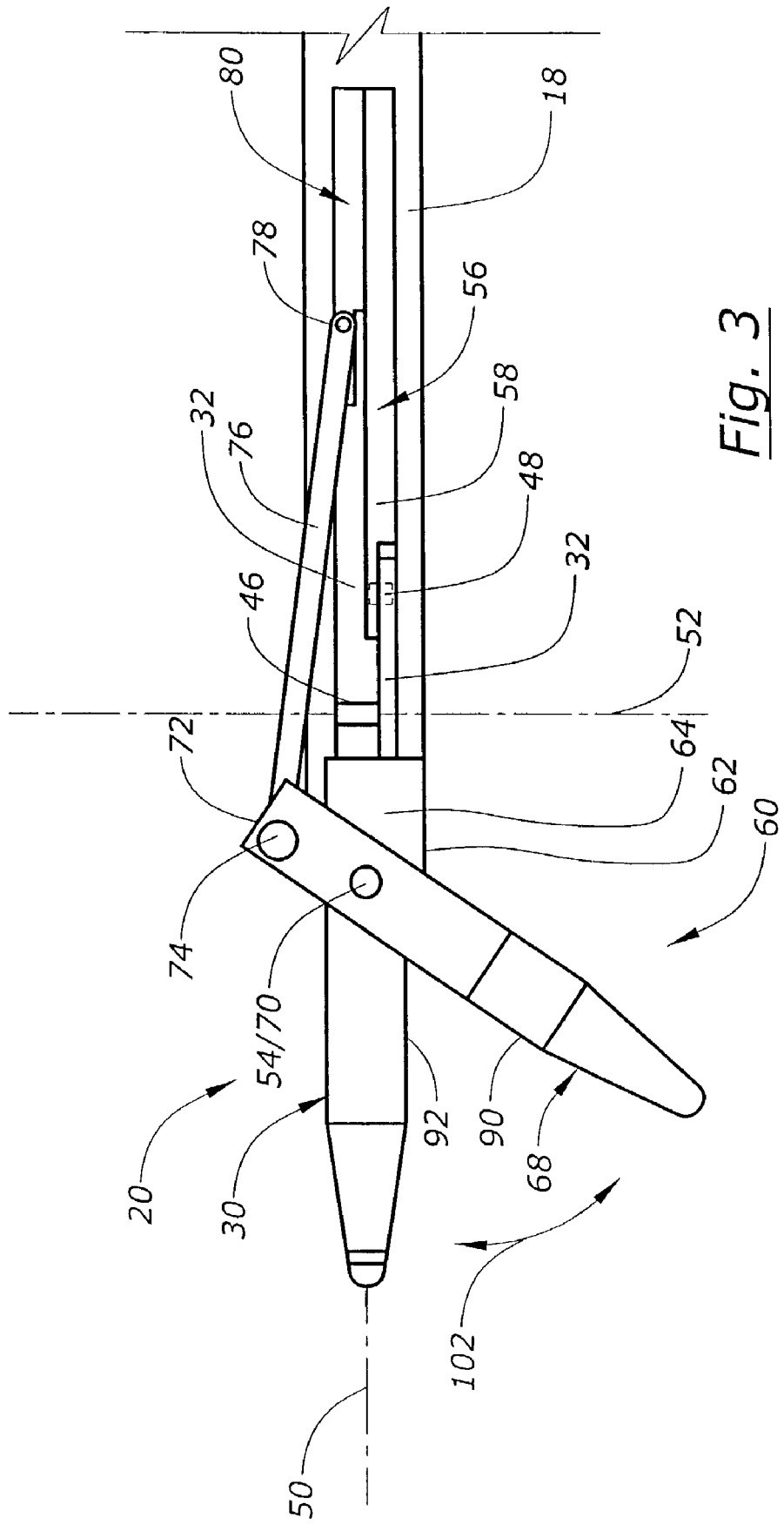

FIG. 3 an enlarged view of the end effector of FIG. 2 but in top plan view and in a second or scissors state (jaws open).

Figure 1:
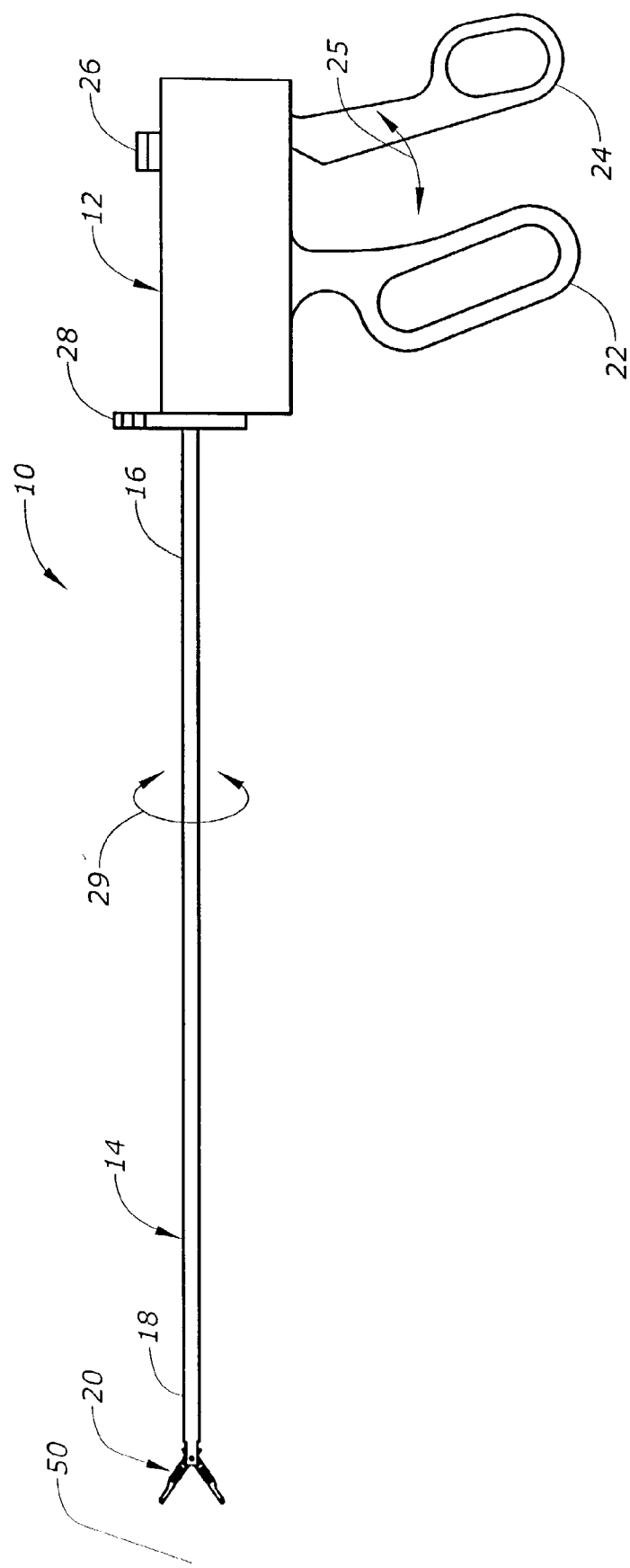
FIG. 1 is an elevational view of a MIS tool with a multi-functional end effector according to one embodiment of the invention.
Figure 4:
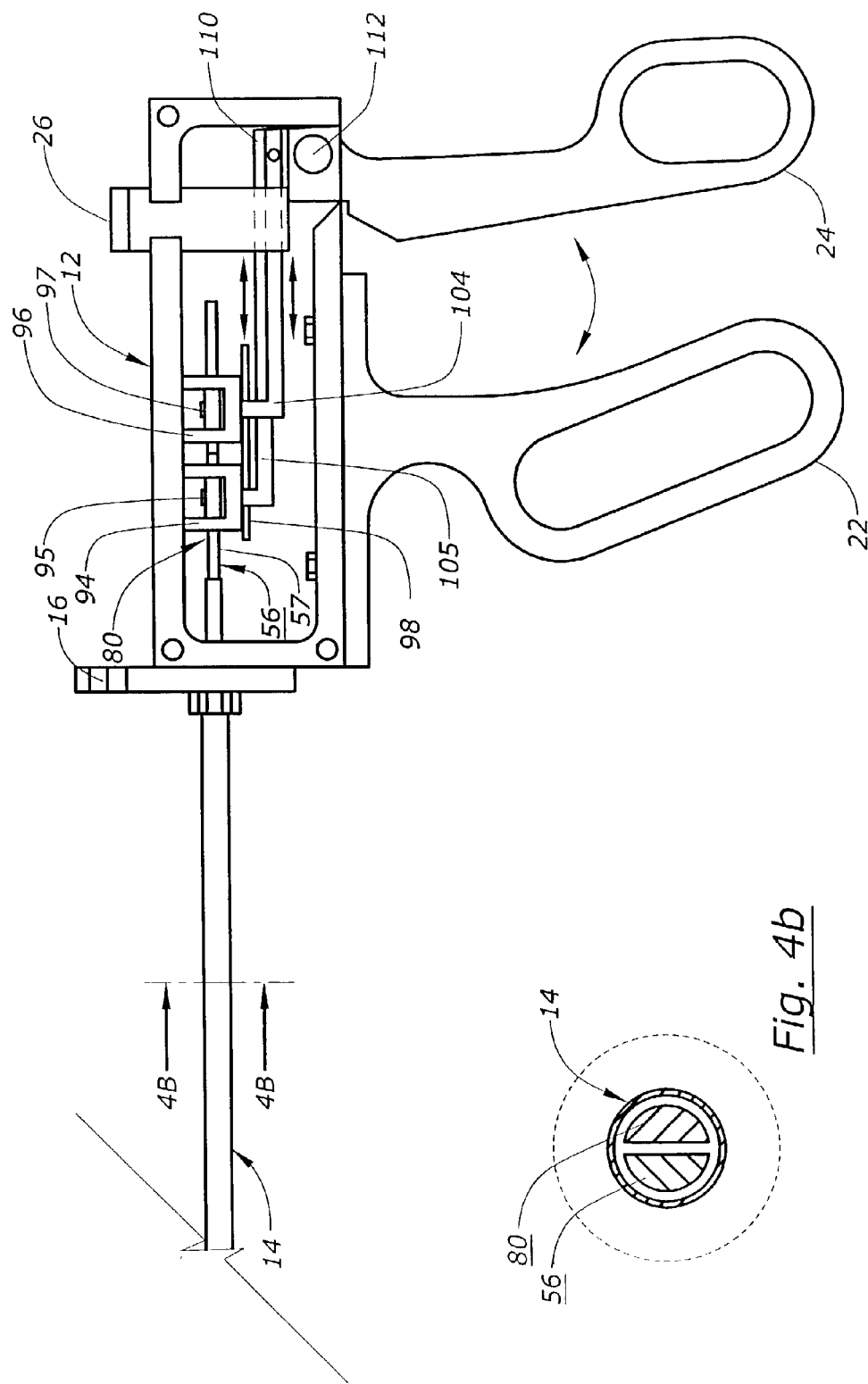

FIG. 4A is an enlarged view of an embodiment of a actuating handle that could be used with the tool of FIG. 1, with portions exposed to show the inner working components of the handle.

FIG. 4B is an enlarged sectional view taken from the perspective of line 4B—4B of FIG. 4A.

Figure 5:
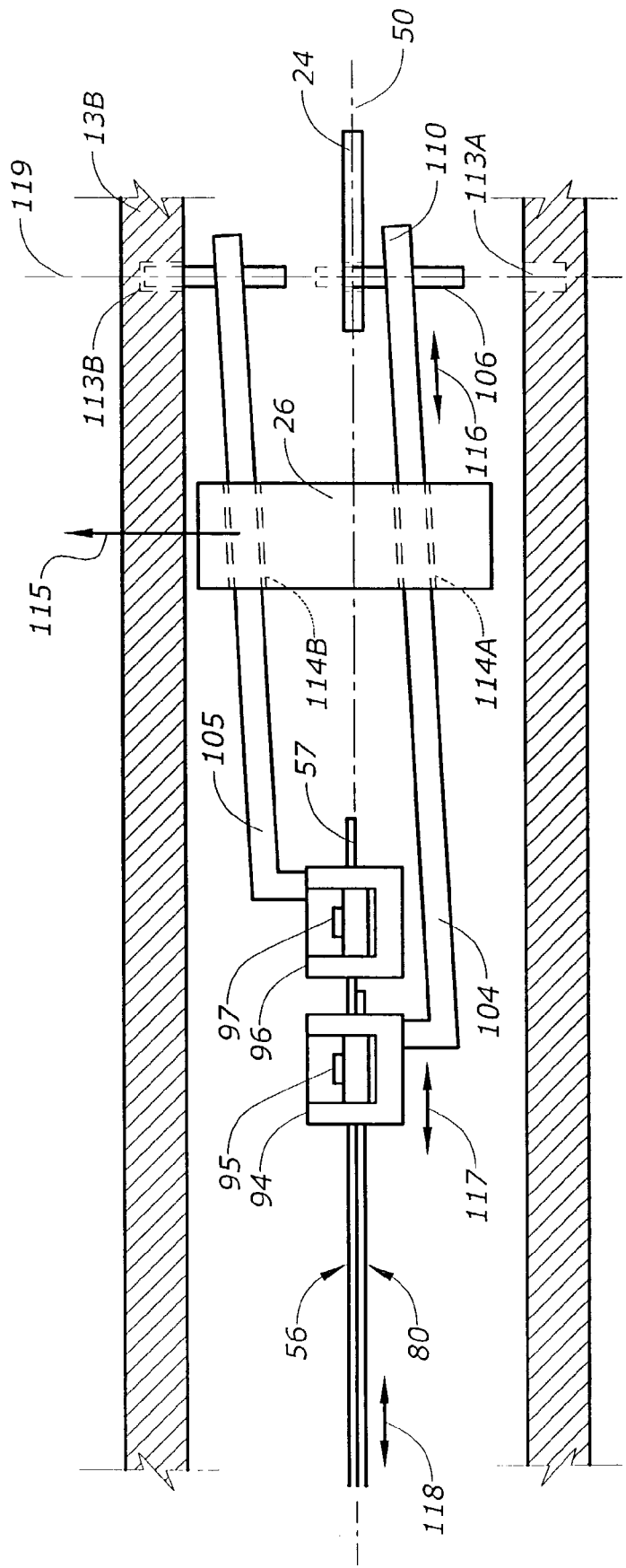
Figure 6:
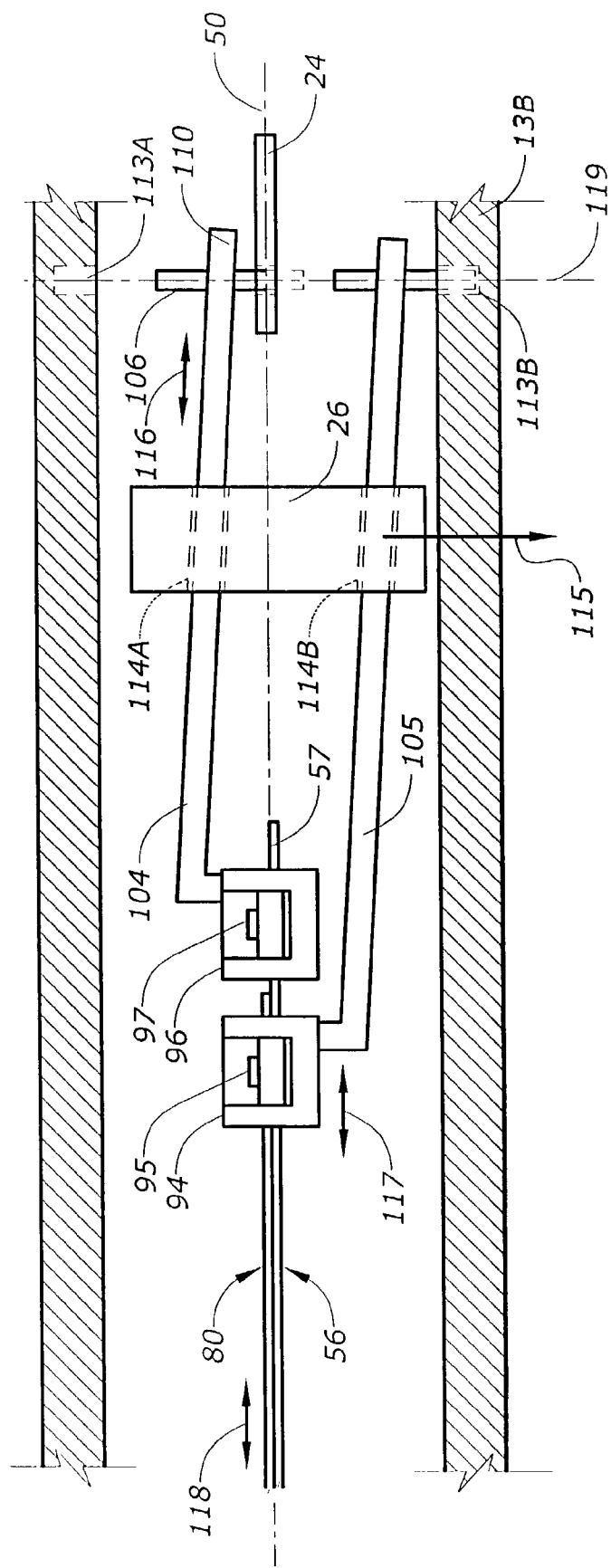

FIGS. 5 and 6 show diagrammatically how selection between multiple functions for the end-effector is accomplished at the handle of FIG. 4A.

FIG. 7 is an enlarged perspective view of an end effector for an alternative embodiment according to the present invention. FIG. 7 shows a compliant mechanism end effector with its jaws in a normal, neutral or unactuated state, where the jaws have grasping surfaces which are separated less than a maximum amount.

FIG. 8 is an enlarged end view of the end effector of FIG. 7.

FIG. 9 is similar to FIG. 7 but shows the grasping jaws actuated to an open position greater than the neutral position of FIG. 7.

FIG. 10 is similar to FIG. 9, but showing the end effector in a grasping state with the jaws in a closed position.

FIG. 11 is similar to FIGS. 7, but shows the end effector in a second, different function state, a scissors state with the distal end of the end effector in an open scissors position.

Figure 12:
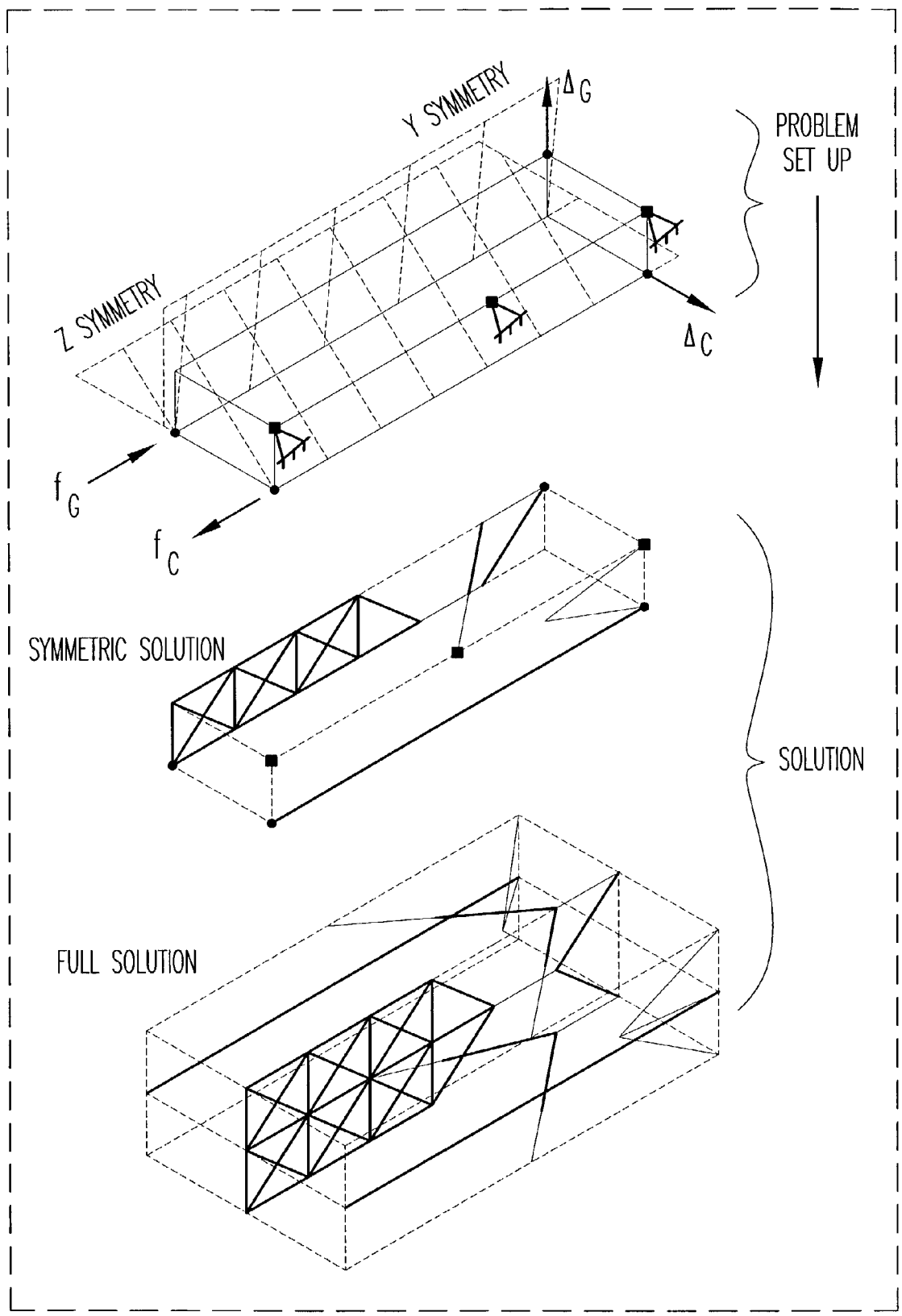

FIG. 12 is a set of diagrams relating to design of the compliant end effector of FIGS. 7–11 by topology optimization.

Figure 13:
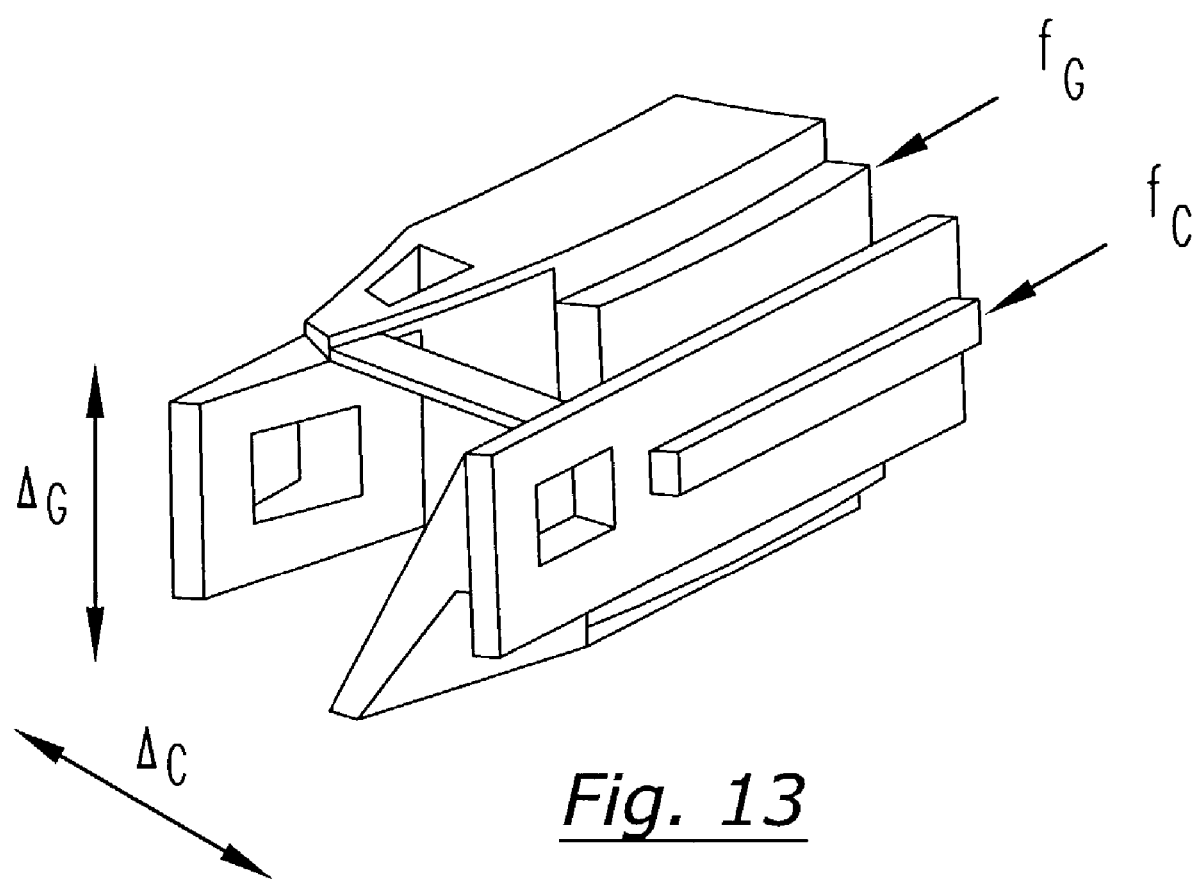

FIG. 13 is a perspective diagram of the initial solid model based on the solution of FIG. 12.

Figure 14:
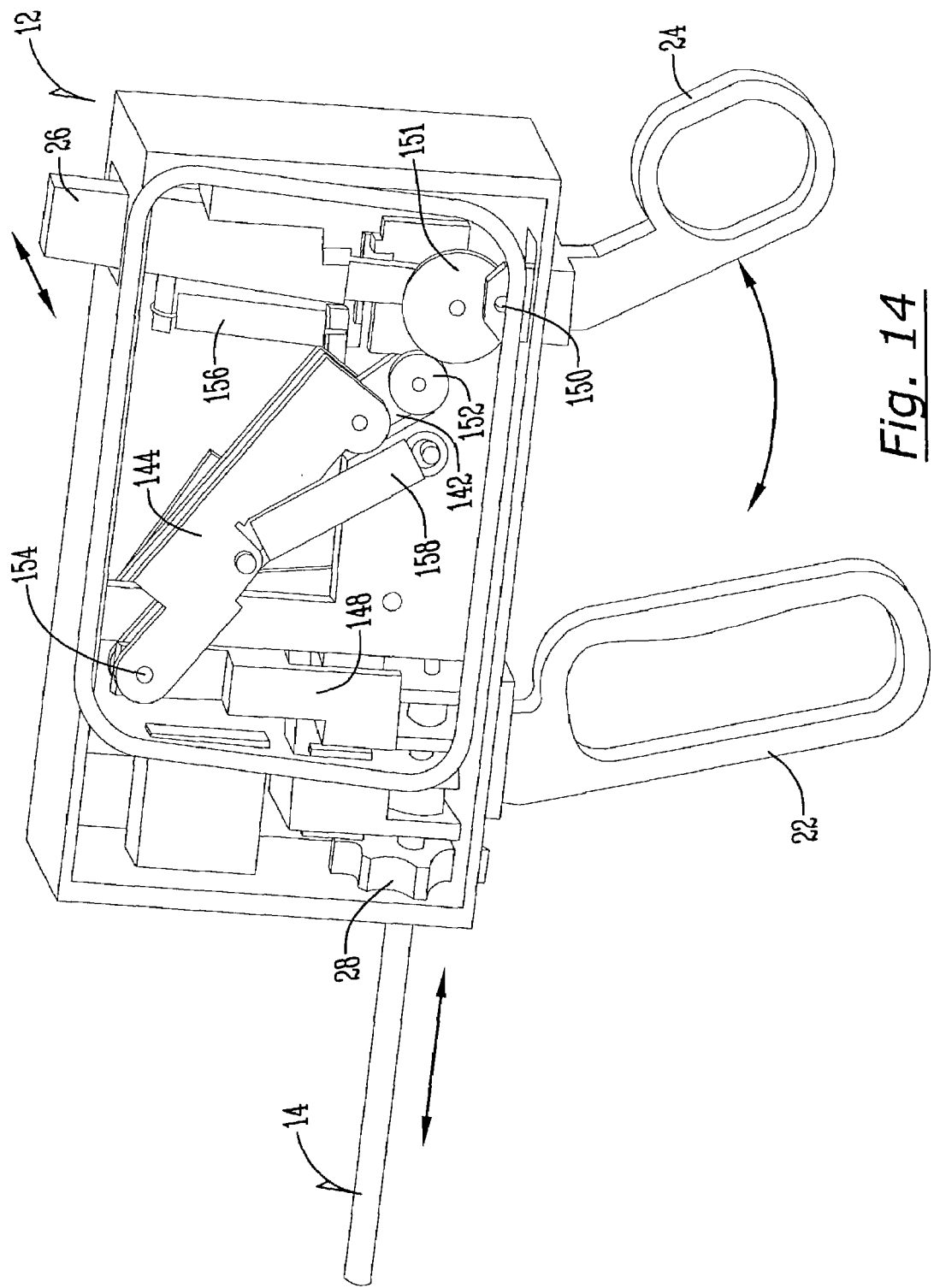

FIG. 14 is a simplified perspective view of a handle design for the compliant end effector of FIG. 7, showing in a cut-away or exposed fashion the inner-actuating components.

Figure 15:
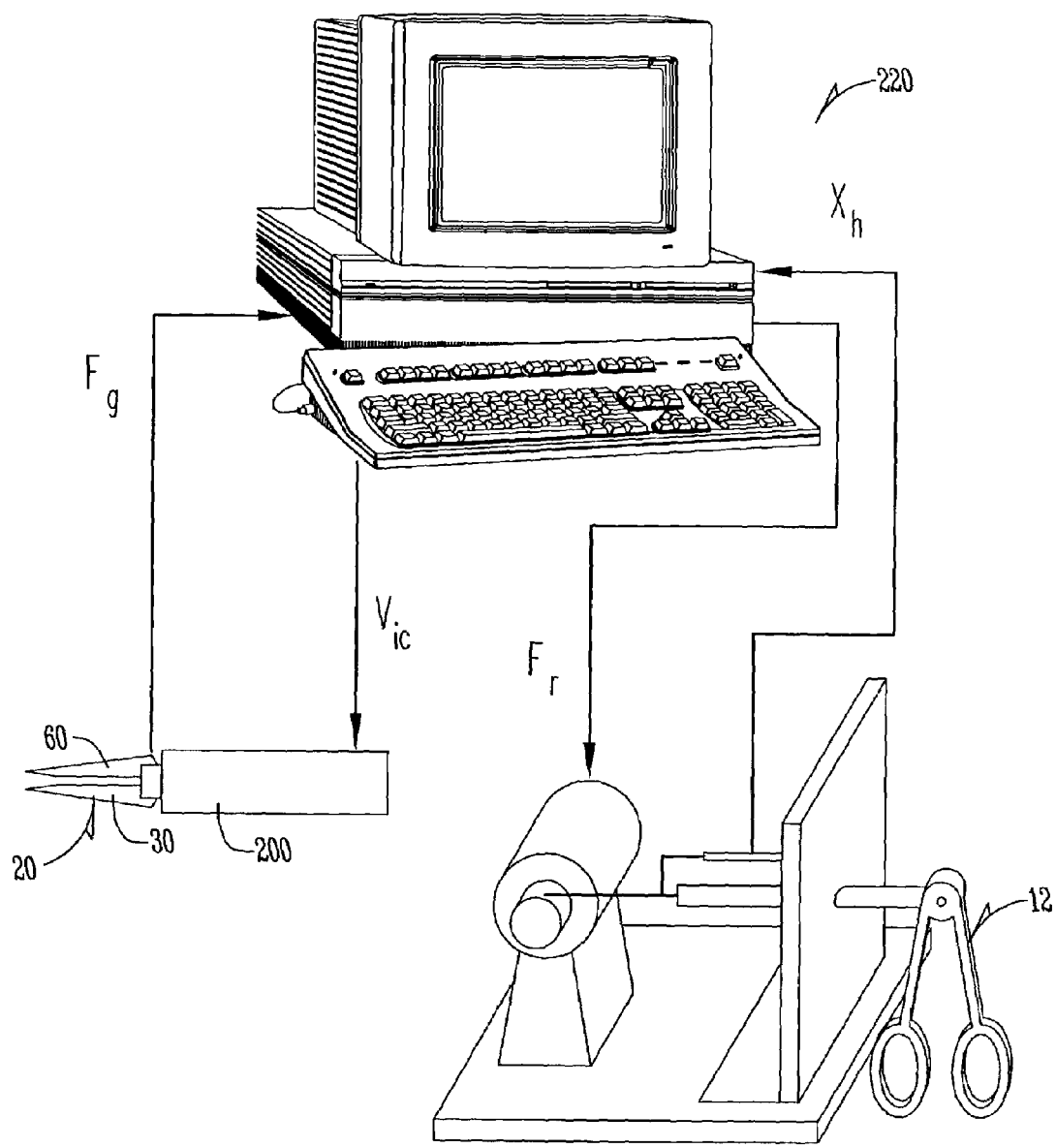

FIG. 15 is a diagrammatic illustration of a system for a semi-robotic use of the compliant end effector such as that shown in FIG. 7 and an electroactive actuator.

Figure 16A:
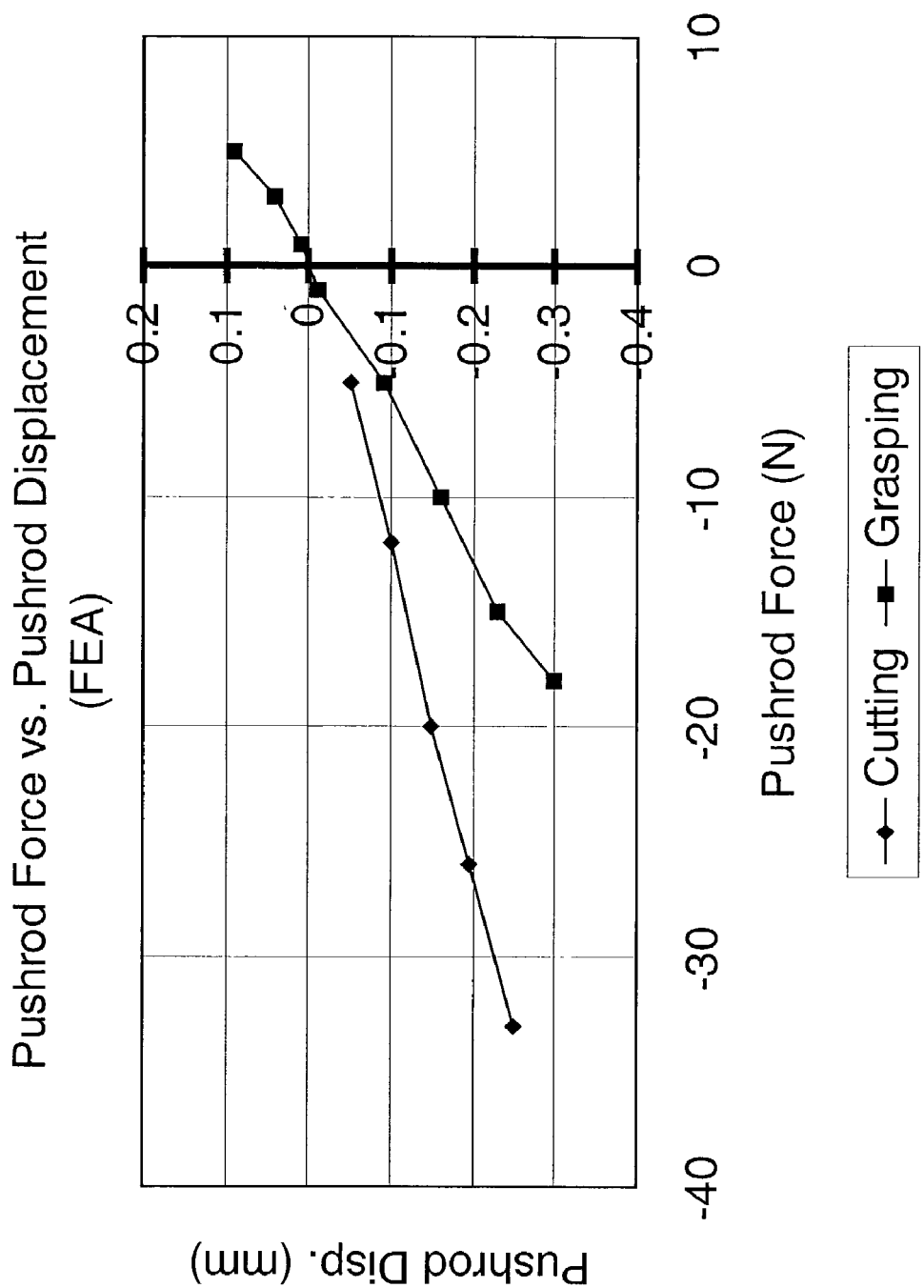
Figure 16B:
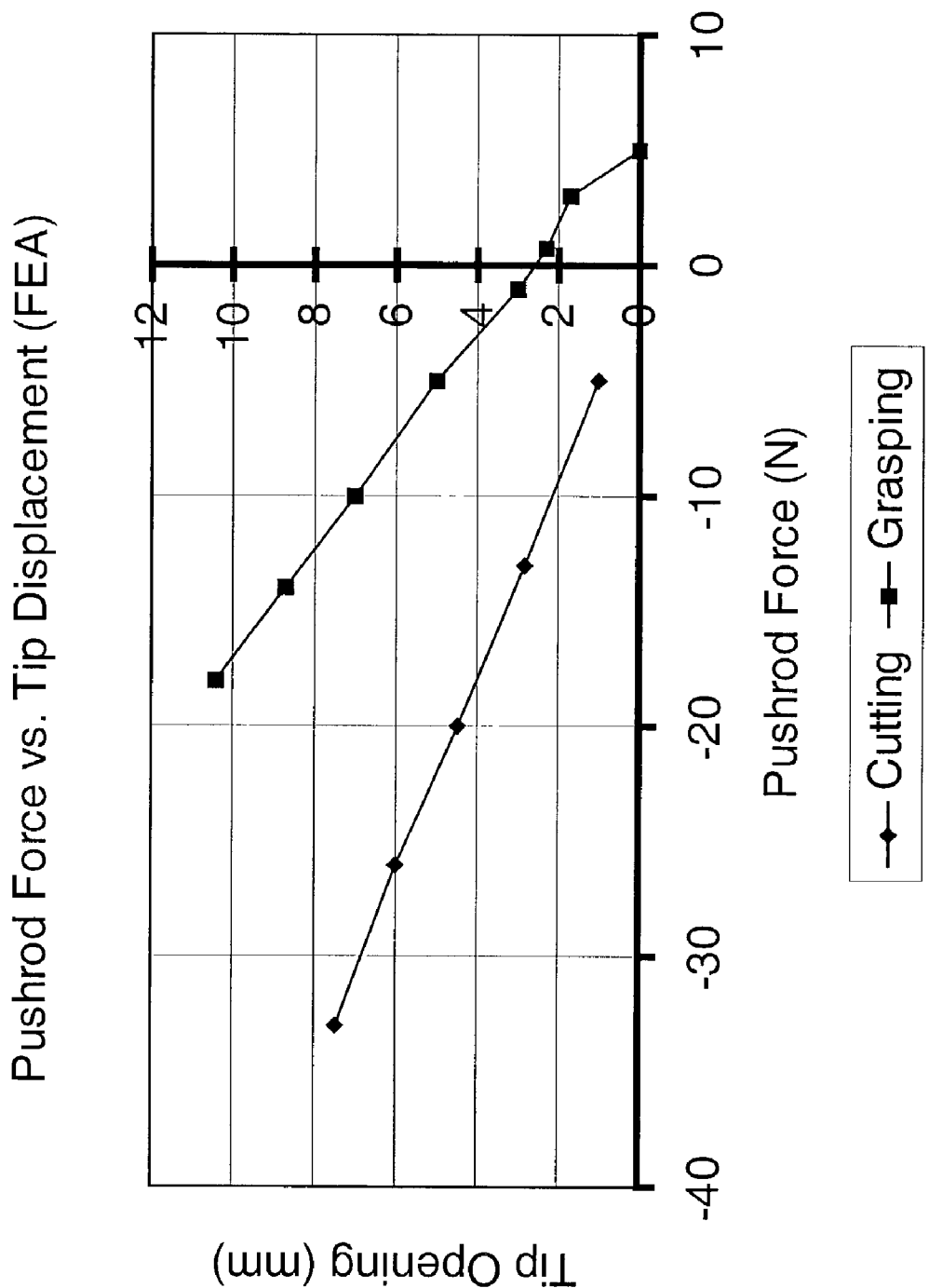

FIGS. 16A and 16B are graphs showing experimental data of a simulated operation of the compliant end effector of FIG. 7.

Figure 17A:
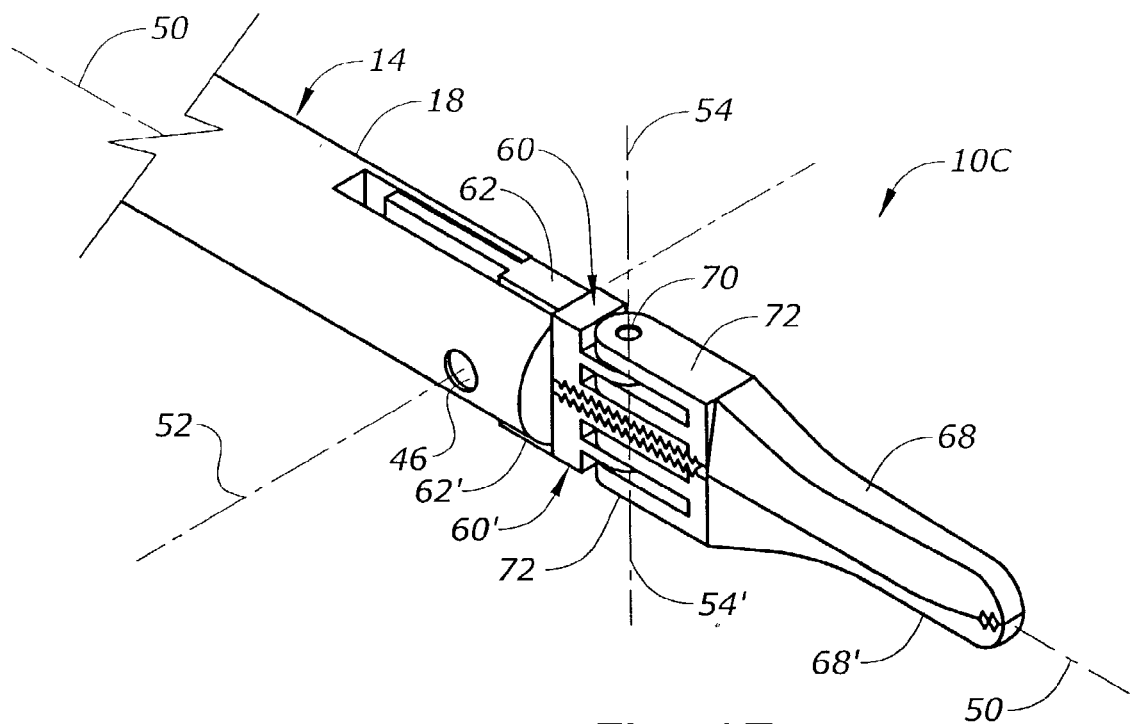

FIG. 17A is an isolated perspective view of a third embodiment according to the present invention, showing a multi-functional end effector comprising grasping and cutting jaws, shown in a grasping state (closed position). The jaws are also articulatable.

Figure 17B:
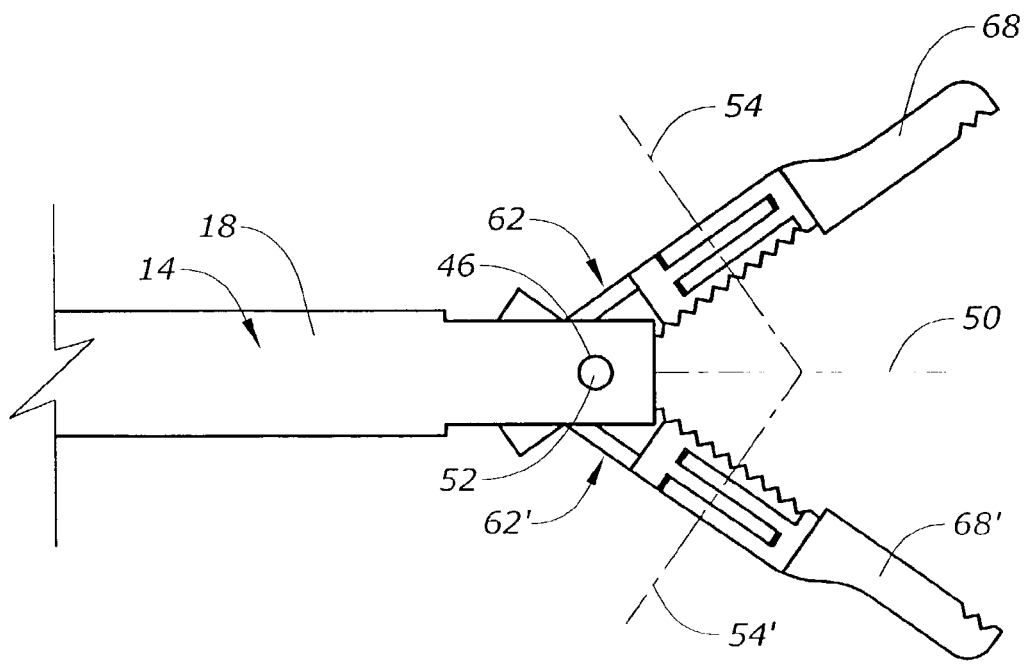

FIG. 17B is similar to FIG. 17A but shows the end effector in a grasping state (open position).

Figure 17C:
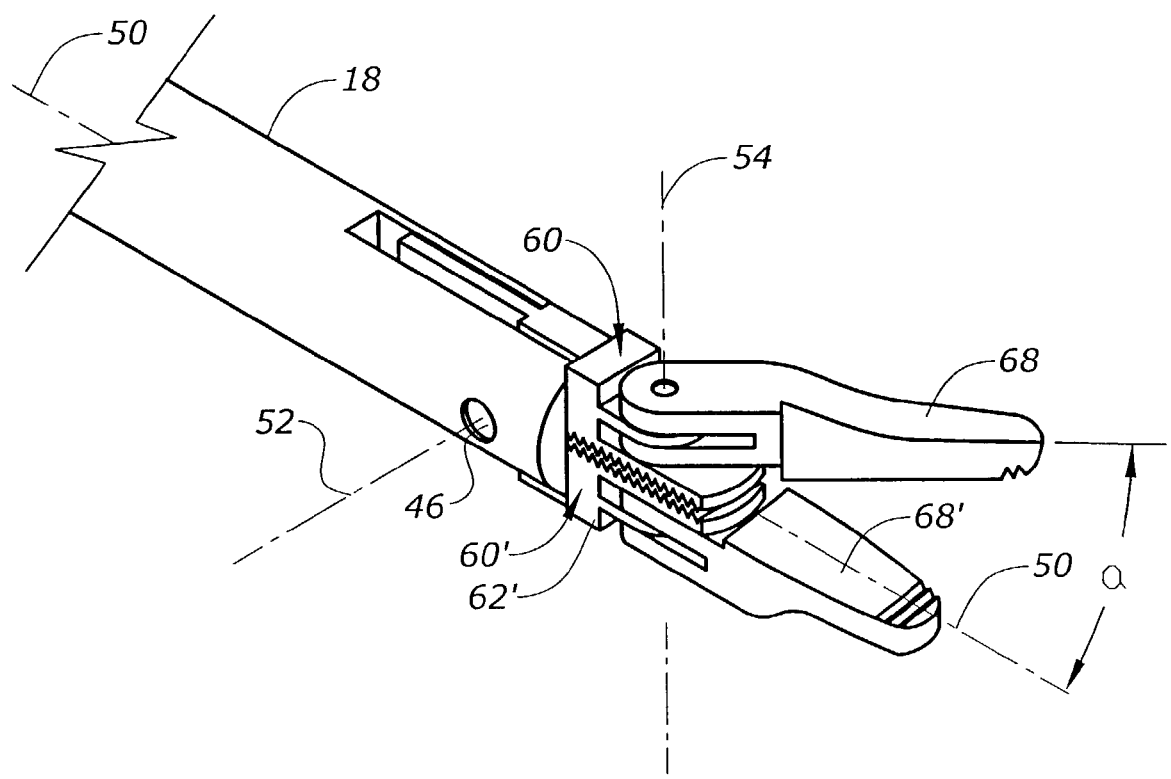

FIG. 17C shows the end effector FIG. 17A converted to a scissors state or mode with the scissoring sections of the jaws in an open position.

Figure 17D:
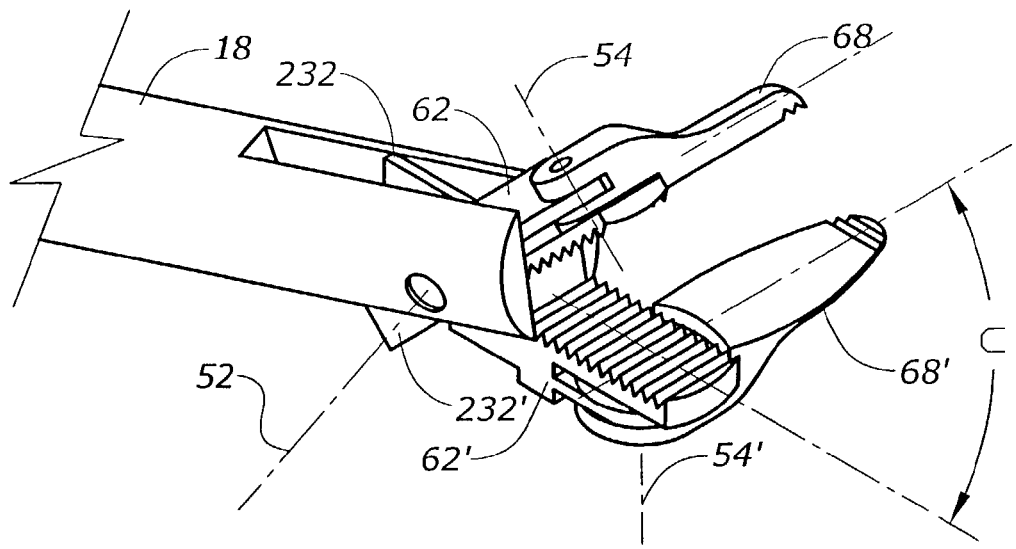

FIG. 17D shows the end effector of FIG. 17A in a third functional position, where distal sections of the jaws are articulated to the side of the centerline of the end effector and the jaws are open in a grasping mode such that the articulated distal sections of the jaws can function as articulated grasping jaws.

Figure 17E:
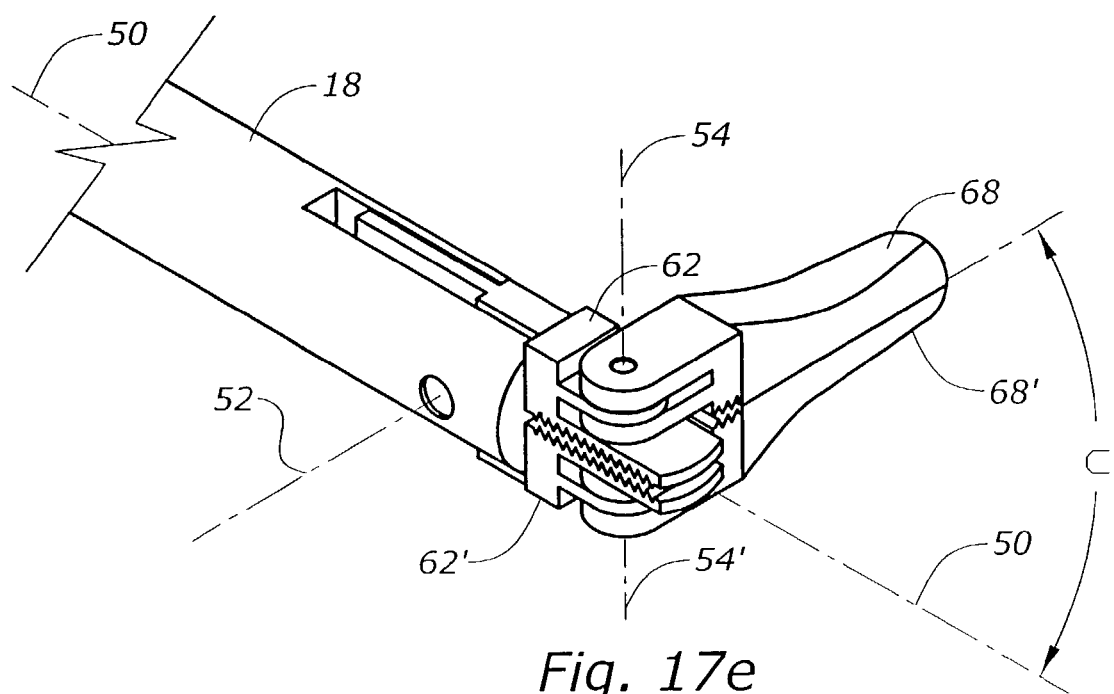

FIG. 17E is similar to FIG. 17D but shows the jaws in a closed articulated grasping position.

Figures 18A, 18B:
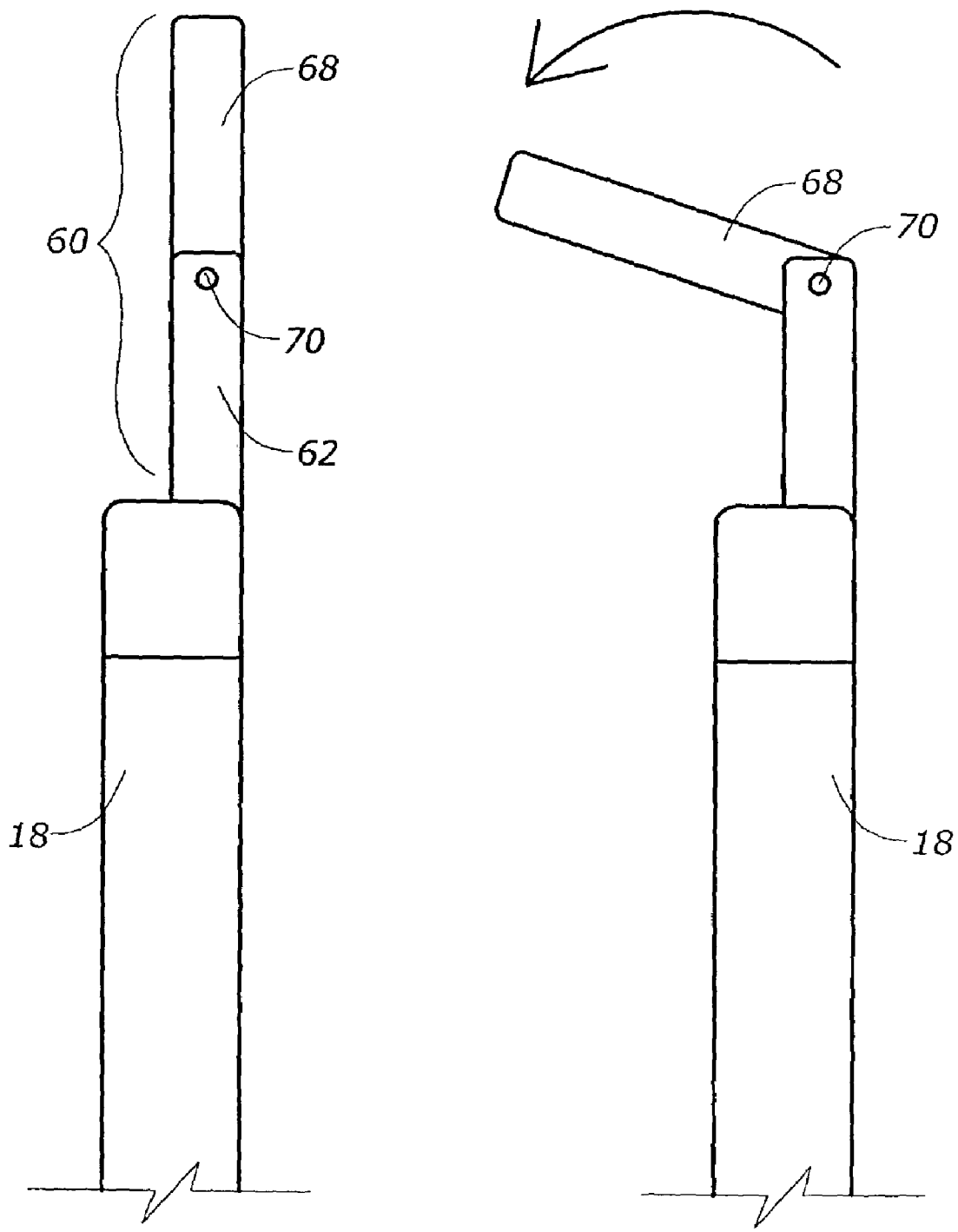

FIGS. 18A–B are simplified diagrams illustrating how the end effector of FIG. 17A–E can function as straight grasping jaws, as scissors, or as articulated grasping jaws.

Figure 18C:
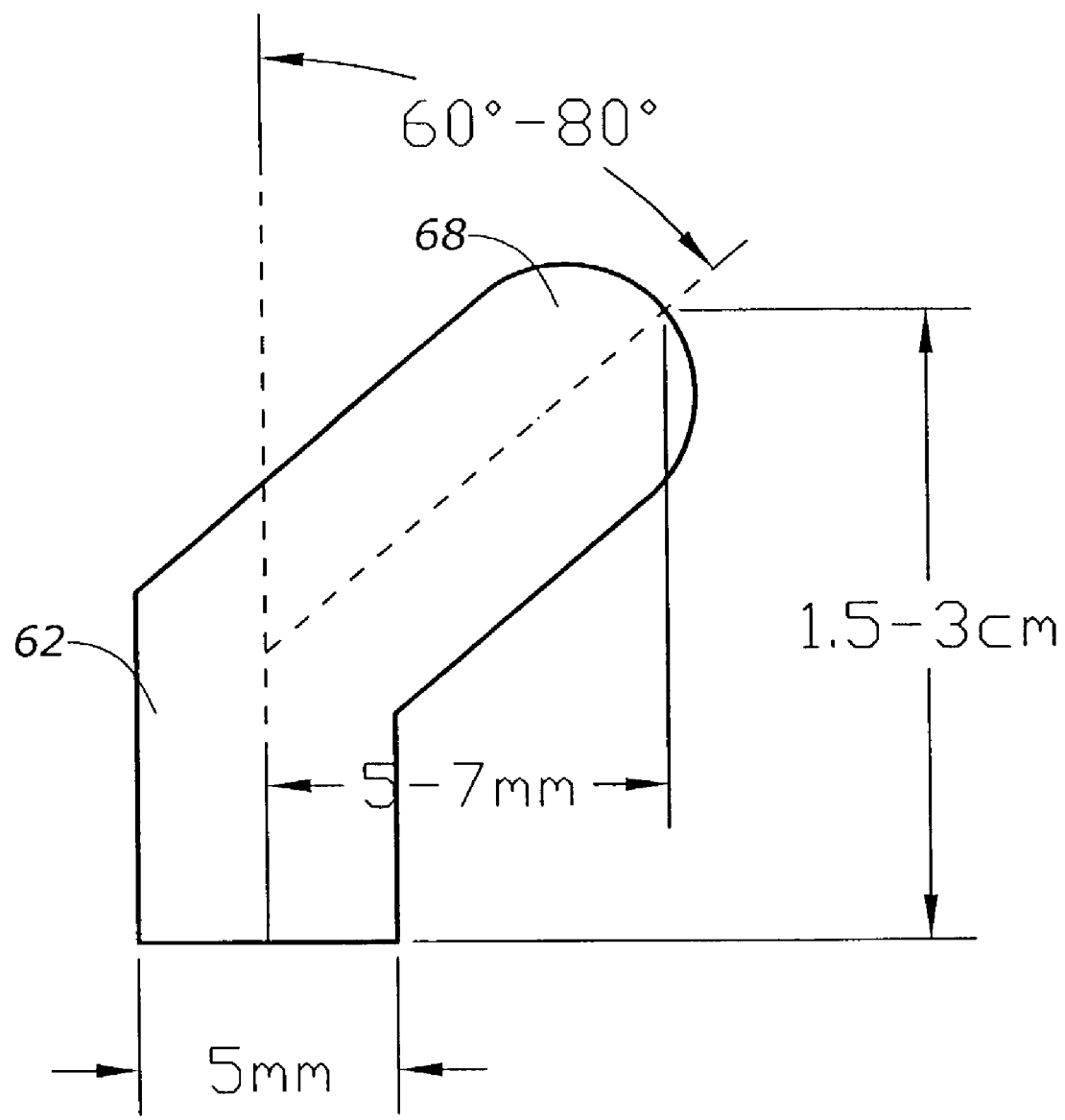

FIG. 18C is a further illustration of articulation.

Figure 19A:
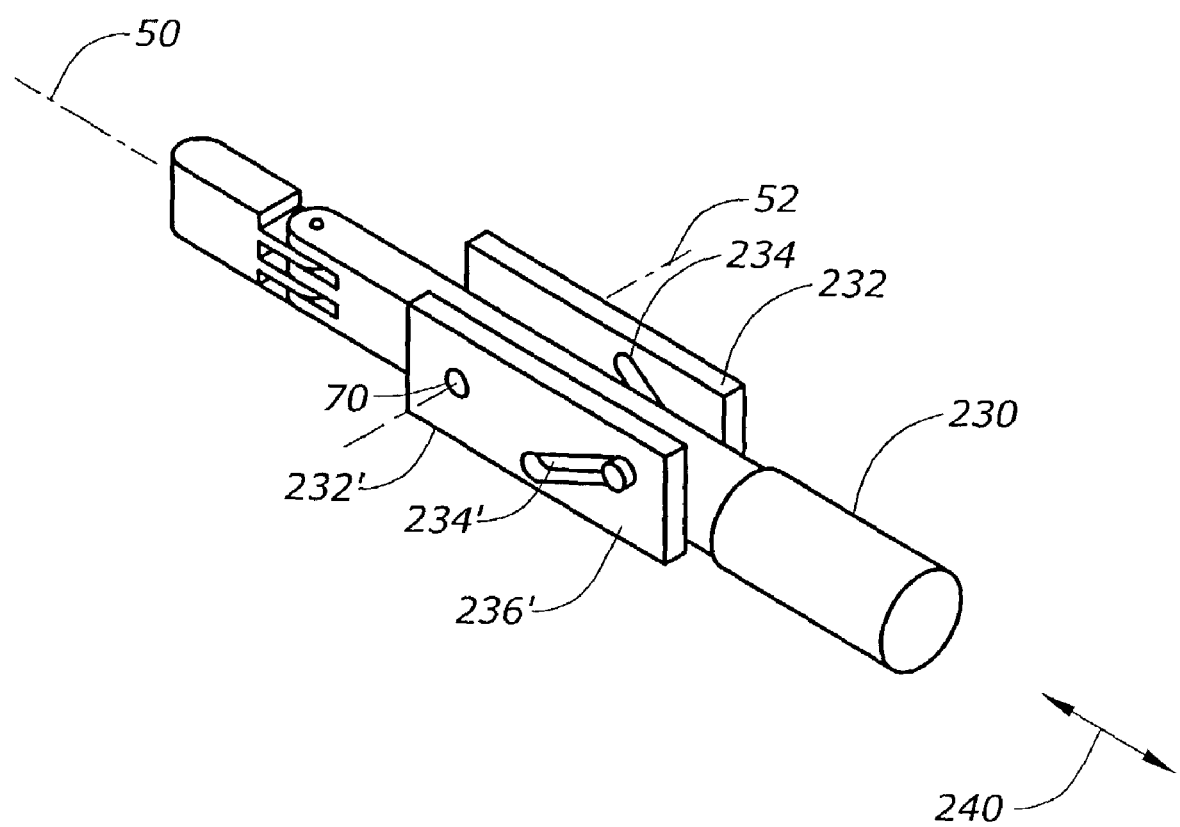

FIG. 19A is a more detailed, enlarged, isolated view of an end effector of the style of the embodiment of FIG. 17A–E, further showing structure for allowing mechanical linkage mechanism grasping actuation of the end effector jaws, illustrating the jaws in a grasping state, closed position.

Figure 19B:
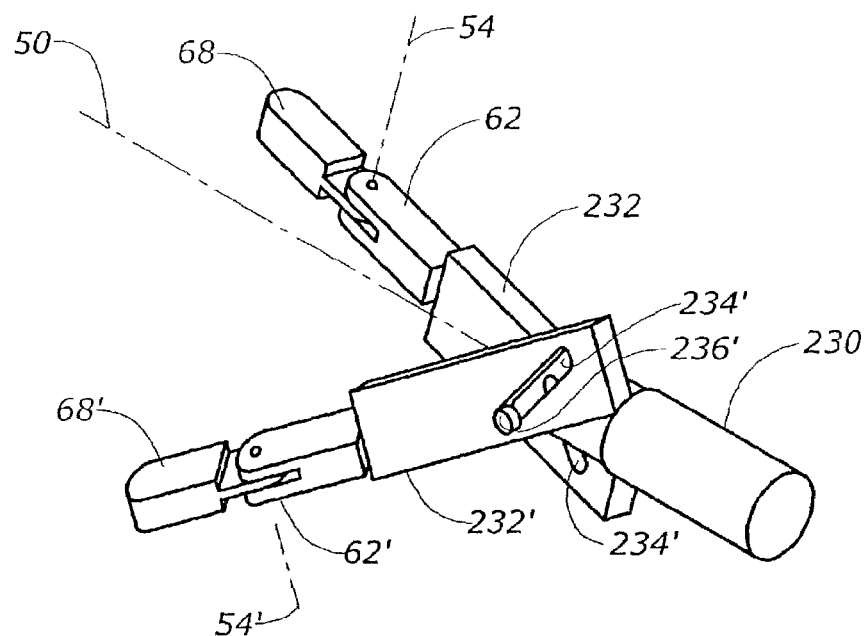

FIG. 19B is similar to FIG. 19A, but shows actuation of the jaws to an open grasping position.

Figure 19C:
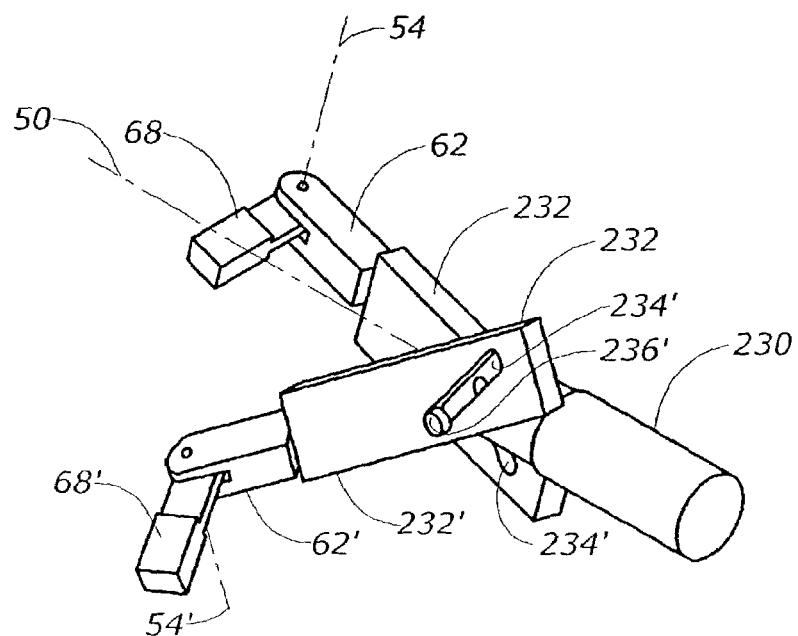

FIG. 19C is similar to FIG. 19B showing actuation of the jaws to an open grasping position with the distal sections of the jaws articulated to the left of the centerline of the end effector.

Figure 20A:
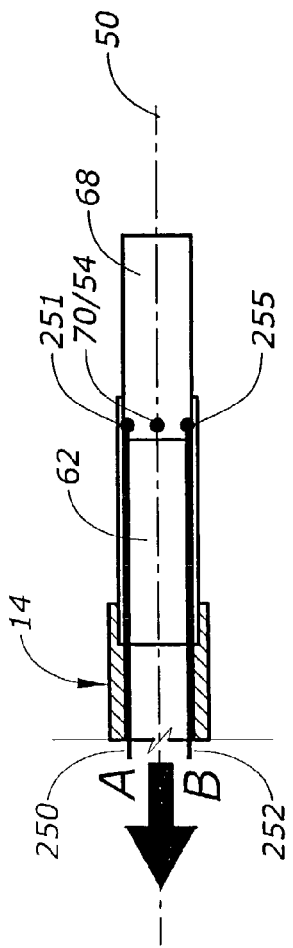
Figure 20B:
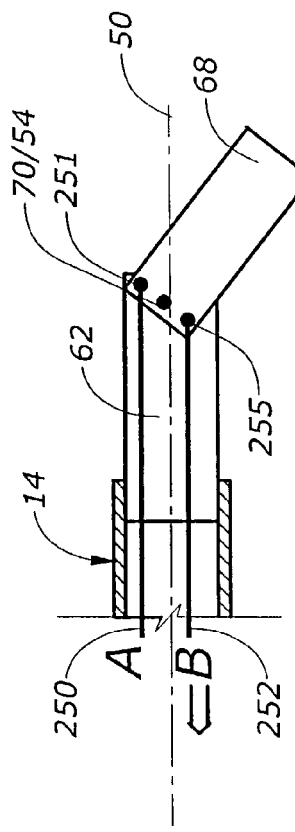
Figure 20C:
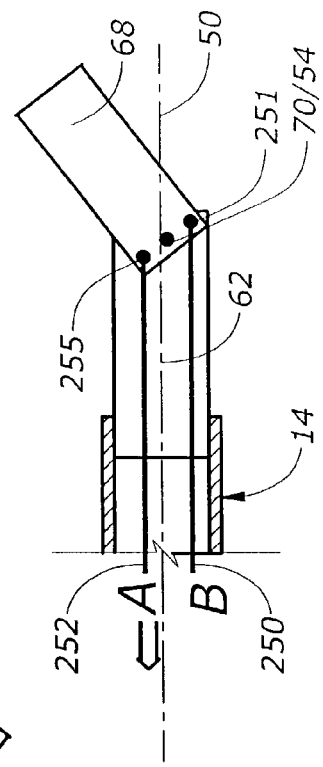

FIGS. 20A–C are simplified diagrams illustrating how side to side articulation of distal sections of jaws through a cabling arrangement can be produced.

Figure 20D:
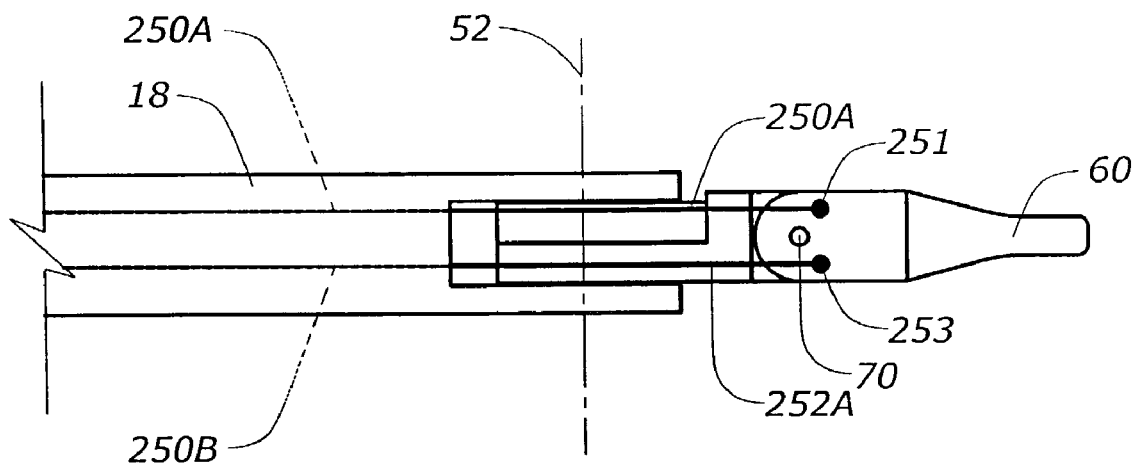

FIG. 20D is a top plan view of the end effector of FIGS. 17A–D illustrating how cabling or wires to the articulatable distal sections of each jaw would be connected.

Figure 20E:
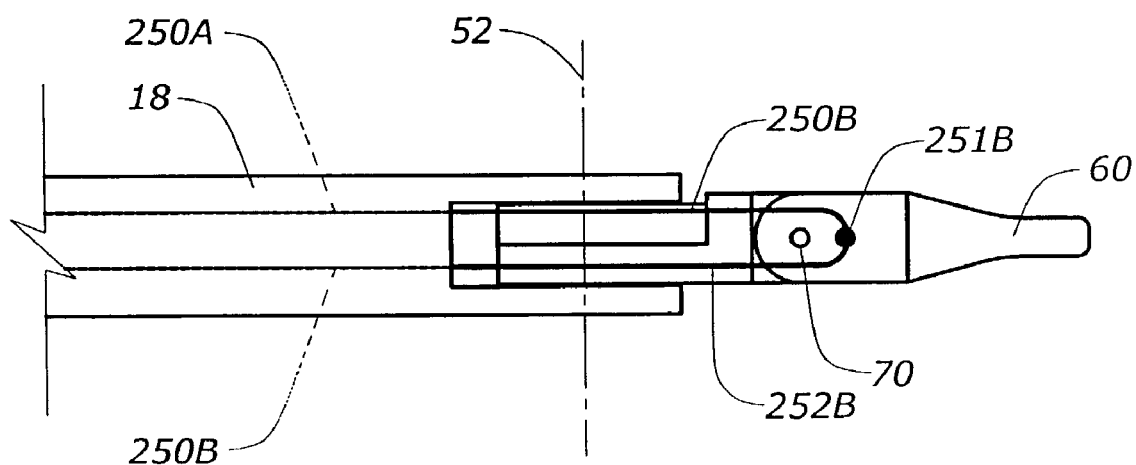

FIG. 20E is similar to FIG. 20D, but shows an alternative cabling connection.

Figure 21A:
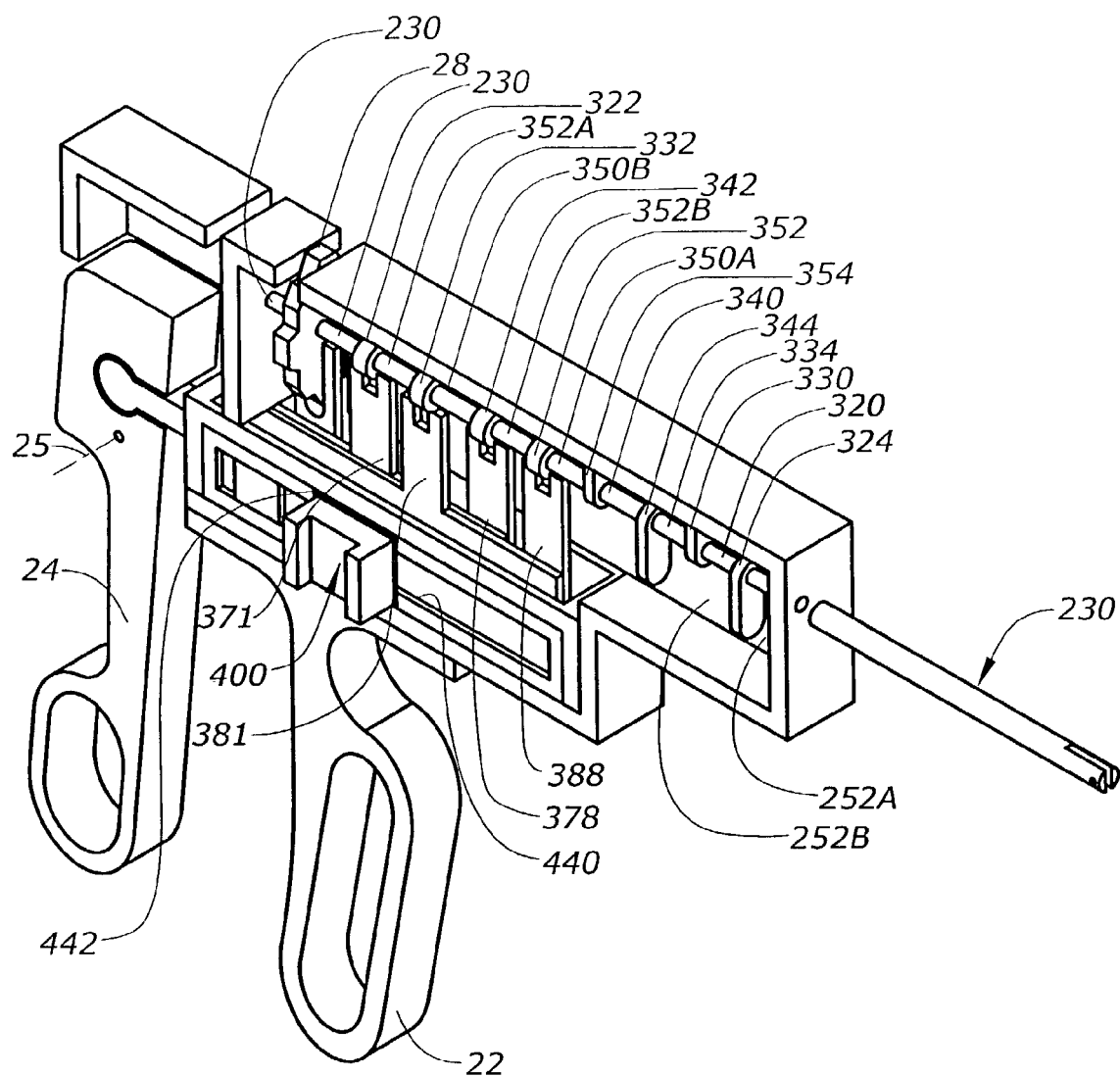

FIG. 21A is an isolated simplified perspective view of handle for the embodiment of FIG. 17A–E, with an exposed view of the interior working components of the handle.

Figure 21B:
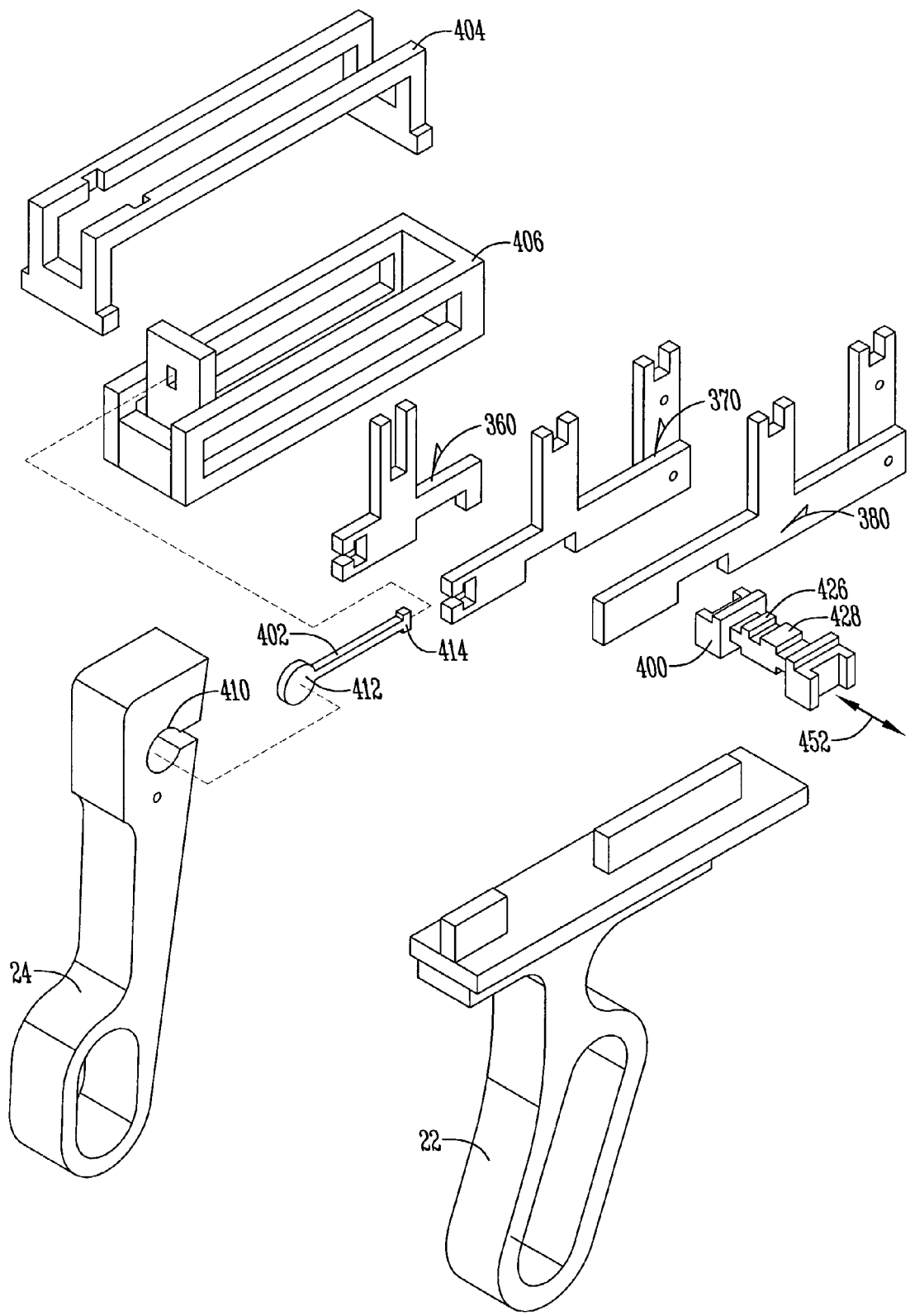

FIG. 21B is an exploded perspective view of some of the interior working components of the handle of FIG. 21A.

Figure 21C:
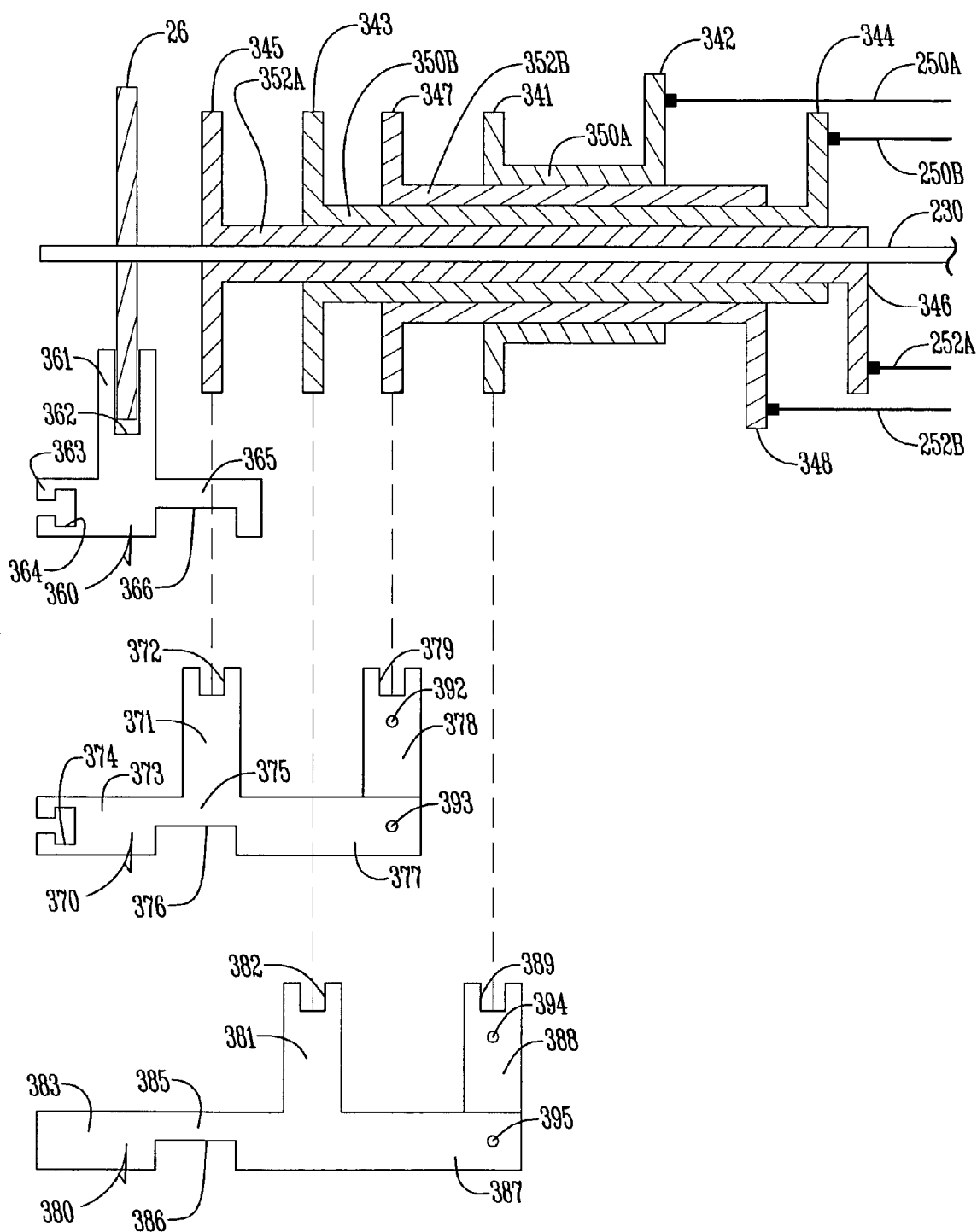
Figure 22D:
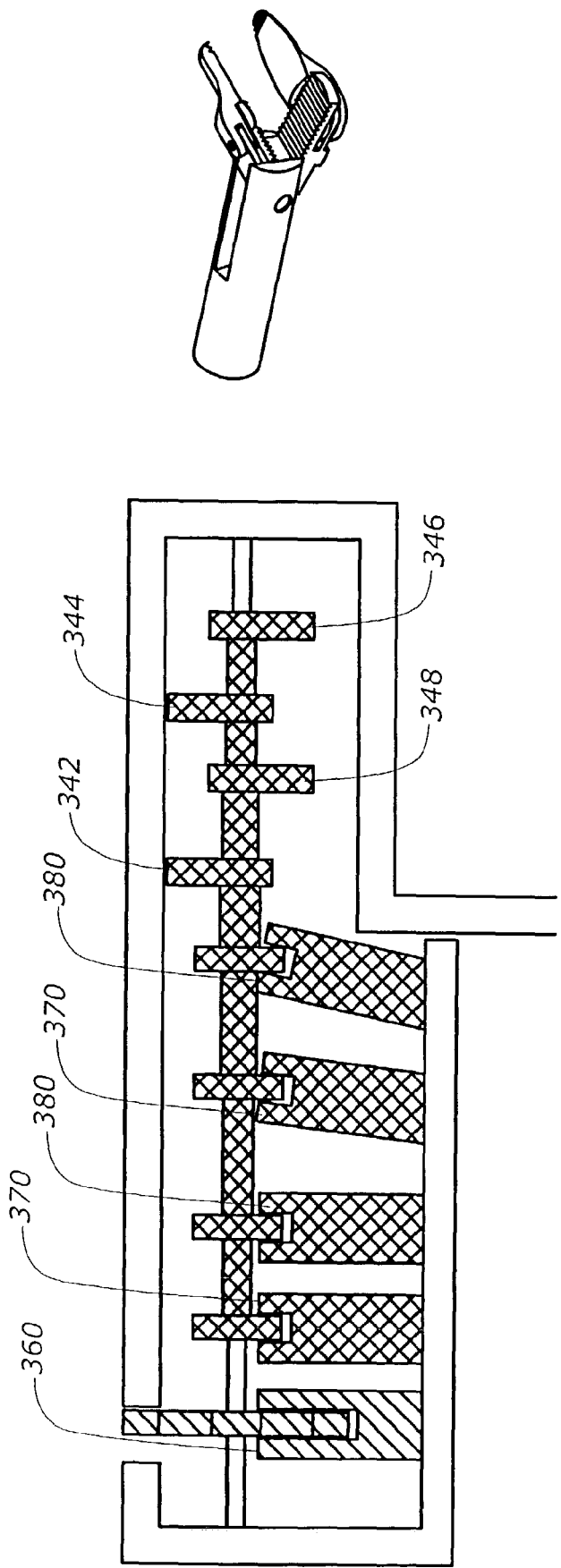
Figure 22E:
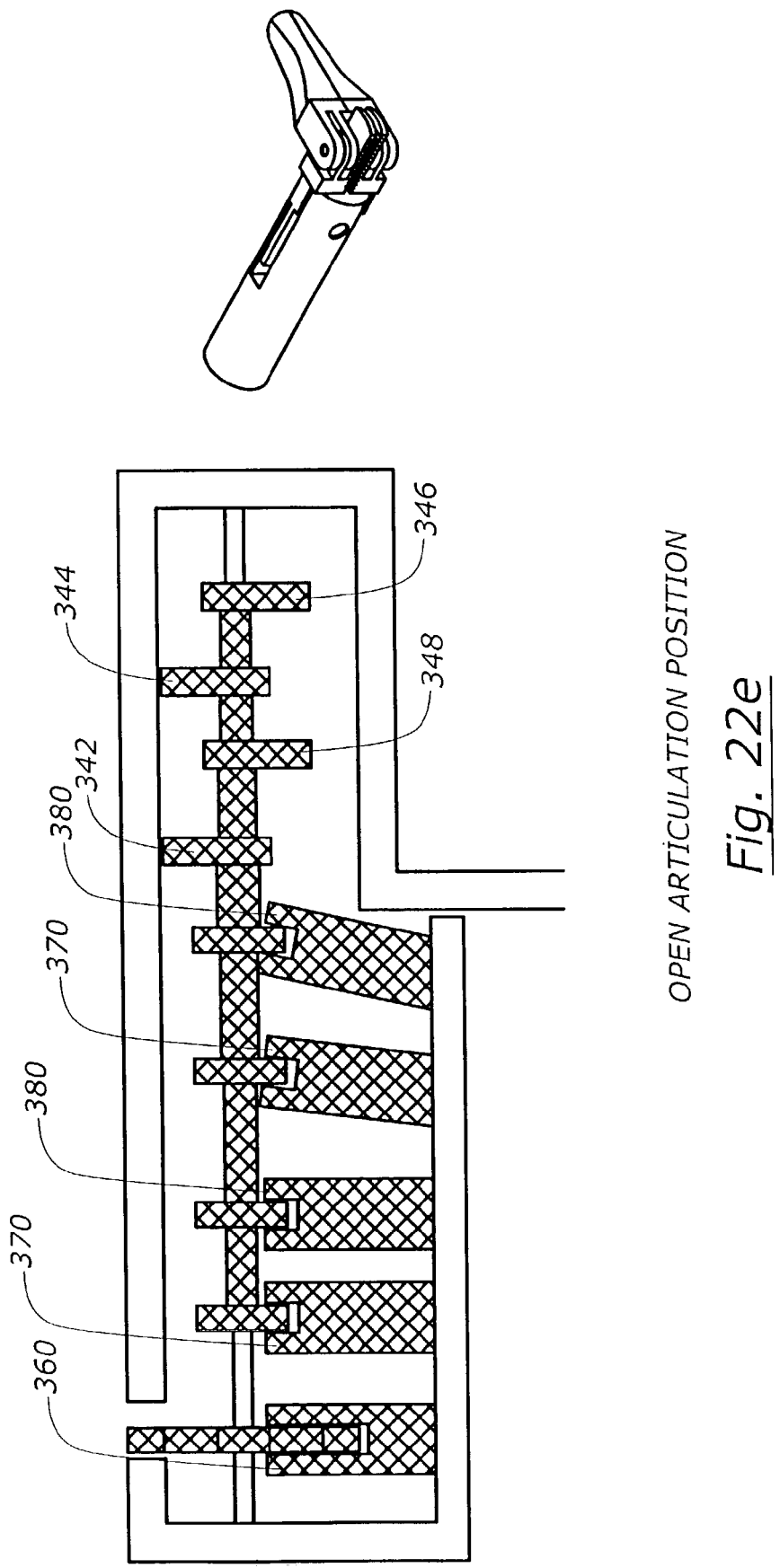

FIG. 21C is an enlarged simplified diagrammatic illustration of some assembled interior working components of the handle of FIG. 21A, and the relationship of such components to other interior working components of FIGS. 21A and B.

FIGS. 22A–E are diagrammatic illustrations of the parts of the inside of the handle of FIG. 21A, illustrating the different configurable modes selectable by the surgeon for different functional modes or states of the end effector of FIGS. 17A–E.

IV. DETAILED DESCRIPTION OF EXEMPLARY EMBODIMENTS OF THE INVENTION

A. Overview

To provide additional understanding of the invention, exemplary embodiments according to the invention will now be described in detail. Some of the exemplary embodiments and the principles related to these embodiments are illustrated in the appended drawings. Frequent reference will be made to the drawings in this detailed description. The same reference numbers will be used to indicate the same or similar parts or locations throughout the drawings unless otherwise indicated.

It is to be understood that these exemplary embodiments are provided for illustration of some of the forms the invention can take, and not by way of limitation.

B. General Apparatus Features and Methods

The general context of the exemplary embodiments will be made with reference to MIS surgery, such as laparoscopy. Most of the embodiments will have at least a multi-function end effector that can grasp or cut by scissors action. These are exemplary of functions of the tool. These functions, as well as additional functions or variations of the functions obvious to those skilled in the art, will be included within the scope of the invention.

Additionally, certain basic design choices are preferred for the exemplary embodiments, but are not limiting to the general invention. For example, for these exemplary embodiments, an outer diameter of five millimeters is chosen such that the tool can fit through a five-millimeter trocar sleeve. Other outer diameters, many bigger than this, are currently in use in the state of the art. This choice was made in response to the trend towards smaller minimally invasive tools. The articulating tip has been chosen to reach a maximum angle of at least sixty degrees. At the fully rotated positions, the tip preferably can be at least five millimeters from the centerline of the tool. The tool preferably meets the general requirement of a total length of between one and half and three centimeters in total length. It preferably grasps a 0.5 mm suture needle or tissue, opens at least 8–15 mm and closes completely. It is preferably between 1 and 3 cm in length, opens or closes in under two hundred ms, and imposes a force sufficient to grasp tissue or a needle. As can be appreciated, these design choices for the exemplary embodiments are not limiting to the invention, and can vary according to design needs and choices.

C. Exemplary Embodiment One (Non-compliant Multi-function Cutting and Grasping)

1. Structure

By referring to FIGS. 1–3, a first exemplary embodiment designed for use as a minimally invasive surgical instrument is shown and will be referred to as mechanism or tool 10. As generally illustrated in FIG. 1, mechanism 10 consists of a handle 12 with mechanical controls, connected to a 32.5 cm long shaft 14 with proximal end 16 and distal end 18, and 5 mm diameter end-effector 20 (shown in open state) at the end of a distal shaft 18. In this embodiment, a surgeon inserts one or more fingers in fixed grip 22, and thumb of the same hand in pivoting grip 24. Relative movement between grips 22 and 24 (here by rotation of moveable handle 24 in either direction indicated by arrow 25) by manual hand movement of the surgeon causes movement of the jaws of end effector 20. These general features are similar to existing MIS tools.

As is also conventional, tool 10 includes a control wheel (rotation knob) 28, also manually manipulatable (rotatable in either direction indicated by arrow 29) by the surgeon with the same hand (e.g. index finger), which in turn causes like rotation of shaft 14 and/or other connecting structure. This allows 360 degrees rotation of the orientation of the jaws of end effector 20.

However, tool 10 is multi-functional in the sense that, depending on the surgeon's positioning of manually selectable switch 26, the jaws of end effector 20 either grasp (or dissect) or cut (by scissors action). The selection, or change in selection, between those two functions or states, can be done quickly and easily by the surgeon, on the fly, and with the same hand as is used to move the jaws of end effector 20.

2. End-Effector

FIGS. 2 and 3 illustrate an end effector 20 in accordance with an aspect of the present invention, and illustrate how grasping and scissors functions can be effectuated from the same end effector 20. First jaw 30 is elongated between a proximal end 32 and a distal end 34, and has a grasping surface 36 (which could have portions serrated), an opposite side 38 from the grasping surface, and opposite side walls 40 and 42 between grasping surface 36 and side 38. Jaw 30 is pivotable about pivot axis 52 defined by pivot pin 46, which is insertable and held in place as shown in distal end 18 of shaft 14. Pivot axis 52 crosses at or close to, and is orthogonal with, central or longitudinal axis 50.

Proximal end 32 of jaw 30, on the opposite side of pivot axis 52 from grasping surface 36 of jaw 30, is a pin-in-slot joint connected by a pin 48 to the distal end 58 of a tube or sub-shaft 56 extending from a proximal end 57 in handle 12 through the interior of shaft 14. Movement of sub-shaft 56 along longitudinal axis 50 of shaft 14 causes proximal end 32 of jaw 30 to displace from axis 50, but also change relative fore or aft position along axis 50, which in turn causes jaw 30 to pivot about axis 52 aligned with axis 50, and thus move between a closed position, such as shown in FIG. 3 (near and in alignment with axis 50), and an open position shown in FIG. 2, extending at an angle from axis 50 (see arrow 100 of FIG. 2). Movement of jaw 30 from closed towards open position is effectuated by moving sub-shaft 56 in a proximal to distal direction. Movement of sub-shaft 56 in an opposite direction moves jaw 30 from open towards closed.

Second jaw 60 has two pieces or sections. A fixed section 62 has a proximal end 64 fixed to the end of shaft 14 (e.g. welded, pinned, set screw, etc.) and a distal end 66 that extends parallel to axis 50. A moveable section 68 is pivotally connected by pivot pin 70 to fixed section 62 and can pivot about axis 54. Pivot axis 54 crosses at or near, and is generally orthogonal to, axis 50, but is also generally orthogonal to axis 52.

Moveable section 68 has a proximal end 72 that is pivotally connected by pin 74 to link arm 76, which is itself pivotally connected by pin 78 to the distal end 84 of a second tube or sub-shaft 80 extending from its proximal end 82 in handle 12 through the interior of shaft 14. Pin 74 is on an opposite side of pivot axis 54 from distal end 73 of section 68, and is also to one side of the longitudinal axis of section 68. As can be appreciated, longitudinal movement of sub-shaft 80 causes moveable section 68 of jaw 60 to move between a position generally aligned with axis 50 (see FIG. 2) to a position pivoted angularly to axis 50 (see FIG. 3). If section 68 is in the position of FIG. 2, movement of sub-shaft 80 in a proximal-to-distal direction in shaft 14 causes link arm 76 to push proximal end 72 of section 68 out to the side of axis 50 (see FIG. 3), which causes distal end 73 of section 68 to swing away from axis 50 in an opposite direction (see FIG. 3). Section 68 can be moved back to alignment over jaw 30 by reverse movement of sub-shaft 80.

As can be seen, sections 62 and 68 of jaw 60, when aligned, approximate the length and shape of jaw 30, and have grasping surfaces that align with similar surfaces on jaw 30. But further, jaw 30 has a sharp edge or blade 90 along a portion of a side margin of its grasping surface 36. Blade 90 is in alignment with a sharp edge or blade 92 (when jaws 30 and 60 are brought together) on an opposite side margin of the grasping surface of jaw 60; in particular, along a side margin of moveable section 68 of jaw 60. Thus, by appropriate design, blades 90 and 92 can pass one another in very close proximity, or even in frictional abutment, to provide cutting by scissors or shearing action, by closing jaws 30 and 60 (by pulling sub-shaft 56 proximally) and reciprocating sub-shaft 80.

Components for end effector 20 are preferably surgical quality metal (e.g. stainless steel, titanium, etc.). Wire electrical discharge machine (EDM) or metal injection molding processes are attractive fabrication methods, because of the small feature sizes involved. Some exemplary dimensions and specifications for one example of tool 10 are as follows:

| Component | Length |
| --- | --- |
| Jaws (Total length, non-articulated) | 15 mm |
| Jaws opening distance at distal ends for grasping | 15 mm |
| Scissors blade length | 7 mm |
| Scissors opening distance at distal ends | 10 mm |

3. Handle

End effector 20 could be actuated through traditional mechanical means such as tendon wires or push rods, which could be used with linkages similar to those in existing MIS tools. Many current tools have the surgeon manually open or close a handle that applies tension to a tendon wire. The wire then actuates a slider/crank mechanism that opens or closes the jaws. A tension spring could render the jaws normally closed or normally open. Other actuation mechanisms are possible.

Therefore, there are many available choices as to ways to create and translate or transfer movement or force generated at a position away from the end effector, out to the end effector. In the case of tool 10 of FIGS. 1–3, linear push-pull force is used to actuate the end effector 20; in particular, linear push pull force to move jaw 30 in a first plane, and linear push-pull force to move tip 68 of jaw 60 in a second plane.

Alternatively to mechanical actuation, electrical actuation could be used by replacing the tendon wire with, e.g., a piezoceramic actuator, shape memory alloy actuator, or electroactive polymer embedded in or connected to the tool's end effector. A handle similar to those on contemporary MIS tools would then control the amount of voltage applied to the actuation device, which would in turn control the position of the tool's jaws. The latter type of actuation system would also allow for amplified force feedback with the incorporation of a force sensor.

Other types of actuators possible include, but are not limited to, pneumatic, hydraulic, electroactive or combinations of the same, or combined with mechanical and/or electrical components. Therefore, the precise type of actuation can be selected according to design choice or need. One specific example of a mechanical actuator mechanism is shown in FIGS. 1–4, and is now described in more detail.

Referring to FIGS. 1–4, and assuming, in a first case, that jaw 60 is in the longitudinally aligned position of FIG. 2 and that switch 26 is set for clamping action, rotating handle 24 toward fixed handle 22 closes jaws 30 and 60 of end effector 20 (generally in the direction shown by arrow 100 in FIG. 2, in a plane defined by axes 50 and 54). Rotating handle 24 away from handle 22 opens jaws 30 and 60 (in that same plane of arrow 100). The shaft rotation wheel 28 (FIG. 1) is used to change the rotational position of the end-effector about its axis 50. Thus, in this case (the "clamping" state or mode of tool 10), the surgeon sets tool 10 for clamping with thumb switch 26, and can open and close jaws 30/60 for clamping action by changing the relationship of handles 22 and 24 to each other. Jaw 60 is essentially fixed and jaw 30 moves towards and away from it to clamp or dissect. Of course, handle 12 can be moved in three space, to the extent possible given the constraints of MIS, to position end effector 20 inside the patient.

In a second case, assuming jaw 30 is in a closed position (FIG. 3) and switch 26 is set for scissors action, rotating handle 24 away from handle 22 would cause moveable section 68 of jaw 60 to rotate out from axis 50 towards the position in FIG. 3 (generally in the direction shown by arrow 102 in FIG. 3, in a plane defined by axes 50 and 52). Rotating handle 24 toward handle 22 brings moveable section back to jaw 30 (in that same plane of arrow 100). Thus, in this case (the scissors state or mode of tool 10), the surgeon sets tool 10 for clamping with finger switch 26, and can open and close jaws 30/60 for clamping action by changing the relationship of handles 22 and 24 to each other. Here jaw 30 is essentially fixed in place, and jaw 60 moved towards and away from it (although in a different plane than when in clamping mode), to give scissors or shearing action.

As previously explained, multi-function is controlled by which sub-shaft 56 or 80 is moved relative end effector 20. If sub-shaft 56 is moved, jaw 30 pivots and end effector 20 can be used in grasping mode. If sub-shaft 80 is moved, moveable section 68 of jaw 60 pivots, enabling a cutting mode by scissors action. There are a wide variety of ways selective linear actuation of one of two sub-shafts can be accomplished. In this embodiment, rotational movement of moveable handle 24 is translated to linear movement to actuate one or the other of sub-shafts 56 or 80. One example is described with respect to FIGS. 4A–C, which are highly diagrammatical illustrations of the structure and its operation, as opposed to precise, scaled mechanical views.

Each sub-shafts 56 and 80 is a half circular push rod (half-moon shaped in cross-section and oriented through shaft 14 as shown in FIG. 4B). Their proximal ends 57 and 82 are fixed to collars which connect with U shaped brackets 94 and 96 respectively. A set screw, eccentric clamp, or other releasable connector fixes proximal ends 57 and 82 to its respective collar and bracket 94 or 96, which are slideable within handle 12, for example along a track or other retaining structure (shown diagrammatically at ref. No. 98). Thus, if bracket 94 is slid along track 98, only sub-shaft 80 will move linearly. Conversely, if bracket 96 is slid on track 98, only sub-shaft 56 will move.

The toggle switch 26 on top of handle 12 controls whether the tool is in cutting or grasping, i.e. selects between translating rotational movement of handle 24 to bracket 96 or 94. Mechanical links 104 and 105 extend from brackets 94 and 96 rearwardly in handle 12 through channels 114A and B respectively in toggle switch 26, and terminate in free ends that include a transverse pin extending through and outwardly on opposite sides of each free end of links 104 and 105 (see pin ends 106 and 107 for the free end of link 14, and pin ends 108 and 109 for the free end of link 105). A through-hole 110 in the end of handle 24 on the opposite side of handle pivot 112 aligns along an axis 119 when handle 14 is brought to a reference position (e.g. end of travel away from handle 22). Holes 113A and B, in the interior sides of opposite side walls 13A and B of handle 12, also are along axis 119.

Switch 26 is slideable laterally relative to the top of handle 12 between two opposite extremes (here called "right" and "left" relative to the top views of FIGS. 5 and 6). Sliding switch 26 to the right (as shown at arrow 115 in FIG. 5), shifts both links 104 and 105 to the right. In turn, pin 107 of link 104 enters bore 110 of handle 24 and pin 108 of link 105 enters hole 113A of wall 13. Mechanical connection is accomplished between handle 24 and bracket 94, while handle 24 is disengaged from connection to bracket 96 (and, in fact, bracket 96 is locked against movement by link 105 being held fixed to wall 113 by pin 108). Rotational movement of handle 24 would be translated into linear movement (see arrow 116 of FIG. 5) by handle 24's pivotal connection to link 104 by pin 107, which would slide bracket 94 (see arrow 117 in FIG. 5) and thus linearly move half shaft 80 (see arrow 118 in FIG. 5) to operate cutting action for tool 10.

On the other hand, clamping mode is shown in FIG. 6. Sliding switch 26 to the left (arrow 115 in FIG. 6) causes links 104 and 105 to follow to the left and move pin 109 of link 105 into hole 110 in handle 24, and pin 106 of link 104 into hole 113B in opposite handle wall 13B. This locks link 105 to move with movement of handle 14, and locks out link 104 from movement. Movement of handle 24 would be translated to linear movement of link 105 (arrow 116, FIG. 6), which causes linear sliding of bracket 96 (arrow 117, FIG. 6), which causes linear movement of half-shaft 56 (arrow 118 of FIG. 6), which effectuates clamping action of end effector 20. Essentially, one of the U-brackets is locked into place while the other is free to move and is actuated by rotating the moving handle 24. When the toggle 26 is switched, the other set of linkages is locked and the second set is connected to the moving handle. Thus, tool 10 is given multi-function by simple toggle switching between modes or states at handle 12.

The components of handle 12 can be fabricated using standard and CNC milling machines, such as are well known, or by other methods.

4. Lumen or Shaft 14

In this embodiment, both shaft 14 and end effector 20 (when jaws 30 and 60 are closed and aligned along axis 50) are designed to fit in a 5 mm port. But, of course, it can be designed for other sizes of trocars (e.g. 3–12 mm) likewise. Still further sizes are possible.

Sub-shafts 56 and 80 could be adjacent or in abutment through shaft 14. Alternatively, they could be concentric (one or both being tubular). Other configurations are possible.

5. Method of Use

FIGS. 2 and 3 display end-effector 20 of instrument 10 in its various opened positions. The jaw length, opening dimensions, handle control style and location were determined through collaboration with a practicing surgeon. FIGS. 2 and 3 also display the mating surface finishes of the jaws. A textured surface is desirable for grasping; but a smooth, sharp edged surface is needed for cutting. For this reason the front 7 mm section of the jaws are smooth while the rear portion is textured. A small amount of texture was also added at the very distal ends of the jaws to allow for improved grasping ability at the tip.

In one embodiment of the tool of FIGS. 1–3, the following performance features were realized:

| Function | Force |
| --- | --- |
| Grasping force | 1.34 lb. |
| Maximum Handle force | 9.0 lb. |
| Pull-Off Force | 2.5 lb. (using red rubber tubing) |
| Cutting Force | 2.0 lb. |

D. Exemplary Embodiment Two (Compliant Multi-function Cutting and Grasping)

1. Structure

A "mechanism" has been defined as a mechanical device used to transfer or transform motion, force, or energy. A "compliant" mechanism also transfers or transforms motion, force, or energy, but, unlike rigid-link mechanisms, compliant mechanisms gain at least some of their mobility from the deflection of flexible members rather than from movable joints only. Compliant mechanisms are single piece flexible structures that utilize elastic deformation to achieve motion transmission. The rigid-linked mechanism of tool 10 of FIGS. 1–3 could alternatively by implemented in a compliant mechanism.

There are a vast number of ways the end effector 20 could be implemented in a compliant mechanism. A variety of methods of design and manufacture of compliant mechanisms are known. Commercially available software exists to assist in design of passive structures. Software has been developed at for the design of compliant mechanisms. A discussion of the same can be found at Dziedzic, R., Frecker, M., Haluck, R. 2002. Design of Multifunctional Compliant Mechanisms for Minimally Invasive Surgery. Minimally Invasive Therapy and Allied Technologies, incorporated by reference herein.

FIGS. 7–16 illustrate an alternative exemplary embodiment of the invention utilizing a compliant mechanism end effector for multi-function clamping or scissors cutting. This second embodiment, referred to herein as tool 10B, includes generally a handle 12 (e.g. FIG. 14) with actuating mechanism, an end effector 20 with jaws 30 and 60, and a shaft 14 connecting handle 12 with end effector 20.

The general principles of tool 10B are similar to tool 10 of FIGS. 1–3. A user can select between states or modes (clamp or scissors) by finger-operated switch 26 extending out of the housing for handle 12. If clamp mode is selected, rotation of handle 24 towards or away from handle 22 moves facing clamping surfaces of jaws 30 and 60 towards or away from each other. If scissors mode is selected, rotation of handle 24 towards or away from handle 22 moves blades 90 and 92 in the sides of jaws 30 and 60 towards or away from each other. A rotation control or wheel 28, fixed to shaft 14, allows the surgeon to rotate the end effector about axis 50 of tool 10B. Differences from tool 10 of FIGS. 1–4 include the following.

2. End-Effector

End effector 20 of tool 10B is a compliant mechanism. It includes what will be called a compliant web 120 of flexible members between an attachment end 122 adapted for attachment to shaft 14, and a distal end 124 which forms an integral junction with jaws 30 and 60.

One difference from tool 10 is that the compliant end effector 20 of tool 10B has what is called a "neutral" position (FIG. 7) for clamping mode, which exists when no forces are applied to proximal end 122. As shown in FIG. 7, the neutral position comprises jaws 30 and 60 spread apart less than (e.g. approximately ½) their maximum distance. The spread is in the plane of axes 50 and 54.

Web 120 here is comprised of multiple flexible members 130A–D between proximal end 122 and distal end 124. The material could be titanium or other surgical grade metal.

In this version, clamping and scissors modes of tool 10B could be produced as follows:

(a) for clamping action:

1) A sub-shaft through shaft 14 which is connected to the proximal end of end effector 20B, can be actuated to apply a predetermined amount of linear pushing force against a point on portion 132 (see FIG. 8) of proximal end 122 of end effector 20B. The portion of 20B including point 132, which is substantially concentric to the portion 134 (FIG. 8), can move relative to portion 134. As a result of such force and movement, the flexible members 130, in combination with a c-shaped member 138, move in such a manner to spread jaws 30 and 60 at distal end 124 of end effector 20B farther apart (see FIG. 9) than in the neutral position (FIG. 7), but in the plane of axes 50/54.

2) A predetermined amount of linear pulling force at point 132 of proximal end 122 would cause flexible members 130 to close jaws 30 and 60 in plane 50/54 (see FIG. 10).

3) Subsequent opening and closing of jaws 30 and 60 could be effected by repeated those steps.

(b) for scissors action:

1) First, portion 132 is pulled to bring the jaws together as in FIG. 10. While holding that position, a sub-shaft through shaft 14 applies predetermined linear pushing force against a point on portion 134 of proximal end 122 of end effector 20B. As a result of such force and movement, flexible members 130 and C-member 138 move in a manner which reconfigure jaws 30/60 into a scissors mode. The scissors neutral position is closed. Instead of further widening jaws 30/60 in the 50/54 plane, such force at that different position would move jaws 30/60 from the closed position of FIG. 10, to a spread position but in the plane of axes 50/52 (see FIG. 11), where blades 90 and 92 formed in opposite side margins of the grasping surfaces of jaws 30 and 60 would be substantially in the same plane.

2) Application of a predetermined linear pulling force against a point on portion 134 of proximal end 122, would then cause convergence of blades 90 and 92 in or near plane 50/52, such that blades 90 and 92 could converge and slightly overlap for cutting action.

3) Release of pulling force would allow jaws 30 and 60 to return to the position of FIG. 11, ready for another cutting stroke or strokes, if desired.

Conversion back to clamping mode could be accomplished by:

1) Applying a predetermined force to point 132 of proximal end 122, which would move jaws 30 and 60 the plane 50/54.

In this example of tool 10B of FIGS. 7–11, the following dimensions exist:

| Component | Length |
| --- | --- |
| Jaws (Total length) | 36 mm |
| Jaws opening distance at distal ends for grasping | 12 mm |
| Scissors blade length | 12.5 mm |
| Scissors opening distance at distal ends in maximum open position | 7 mm |

Thus, web 120 and end effector 20 could essentially be manufactured from one integral piece of material, and utilize the design and compliant features to perform the multiple functions performed by the fixed link mechanism of tool 10.

3. Handle

As indicated by the functional description of compliant end effector 20B, above, certain linear forces can be translated to the end effector to actuate the end effector in at least two different functional modes or states. A variety of methods could be used to translate linear forces, including linear forces of varying magnitude and direction, to the end effector. One example is shown and described with respect to FIGS. 1–4. Two sub-shafts 56 and 80 provide push and pull linear force to two different points or locations at the end effector. The actuating force from handle 12 of FIG. 4 could be used to change direction between push and pull for either sub-shaft, but further, manual actuation through handle 24 can provide variable force to either sub-shaft by the amount of rotational force imparted to handle 24 by the amount of squeezing pressure or separation force exerted by the hand of the surgeon relative to handles 22 and 24.

Another example of an actuation mechanism to supply linear force to the end effector is shown in simplified form at FIG. 14. FIG. 14 illustrates handle 12 with the interior exposed. Handle 12 for tool 10B could be similar to handle 12 described with respect to tool 10. It could deliver linear movement via sub-shafts in shaft 14 which could be used to operate compliant end effector 20 of tool 10B.

A toggle switch 26, like described with respect to tool 10, could determine alignment of the rotational output of handle 24 (could be from a gear arrangement 151, 152 between points 150 and link 142) with respect to one of two linear movement transmission paths through double slider 148. A first transmission path would translate rotational movement of handle 24 via gears 151, 152, to link 144, which would push the top end of slider 148 fore and aft, depending on direction of movement of handle 14. The bottom of slider 148 would be connected to a push rod that sends one source of linear movement to the compliant mechanism. A similar transmission path comprises of a second link 144 and second slider 148 could be connected to a second push rod to a second source of linear movement to the compliant mechanism. The precise arrangement and components to accomplish can vary according to design choice.

According to another aspect of the invention, what is called a static balance mechanism could optionally be included with the actuation system. In the case of a compliant end effector made out of titanium, for example, the compliant design will translate external forces into bending movement determined by the configuration of the flexible members in the compliant mechanism to generate the clamping or scissors actions. Application of a force to overcome the inherent stiffness in the compliant mechanism itself is required, before additional force to generate force at the grasping or scissors jaws. A static balance mechanism equalizing the potential energy due to the inherent stiffness of the end effector, so that the surgeon does not feel or have to overcome the inherent stiffness of material when operating the tool. Springs 158 (and another spring on the other side) shown in FIG. 14 are part of one type of static balance mechanism. By selection of their spring constant, position, and the link lengths and orientations of the transmission path of forces between handle 24 (the input) and the linear output of handle 12, static balance can be achieved.

In the above-described manner, manually actuatable linear forces could be transmitted through shaft 14 to end effector 20 to power the clamping/dissecting or scissors actions of jaws 30 and 60. The conversion between clamp and scissors in accomplished by actuating the toggle switch 26 Thus, FIGS. 7–14 illustrate another exemplary embodiment of a multi-function MIS tool. Static balance could also be added, as described.

a) Piezoelectric Inchworm Actuator for the Compliant Embodiment

The compliant embodiment of the present invention can be actuated by means other than a manual actuator as discussed above. A piezoelectric inchworm may be used as an alternative means of actuation for the compliant grasper-scissors. One possible example is a commercially available inchworm actuator from Burleigh, for example. (See, e.g., http://www.exfo.com/en/products/gf$_{13}$ Family104.asp., Inchworm 800 series).

The compliant tool 10B requires a high actuation force. For instance, the gripper manufactured from titanium requires an actuation force of 10N over a stroke of approximately 0.31 mm to completely close the jaws. In addition, the means of actuation must be small enough to be inserted in tubes currently used in minimally invasive surgery (current tubes often have a diameter of 8 mm). These restrictions make piezoelectric inchworms a candidate for use in actuation of the compliant tool.

The piezoelectric inchworm actuator can be controlled by a computerized control system 220. FIG. 15 shows a schematic of the entire control system for the compliant gripper The position of the instrumented forceps (jaws 30/60), $X_h$, and the force measured at the end-effector (20), $F_g$, are sensed and used to control both the inchworm actuator 200, $V_{1C}$, and the force generation mechanism (not shown) in the user input handle 12, $F_r$. The end-effector 20 and user input device 12 are instrumented with LVDT displacement sensors to measure their position. Through active computer control, the motion of the gripper 20 is precisely scaled-down from the input motion provided by the pair of instrumented forceps 30/60. Local force measurements are obtained through the use of a single piezoelectric element present in the actuator, which is wired separately from the rest of the piezoelectric stacks. In this way, the element may be used continuously as a force transducer. The resulting signal must be filtered to remove unwanted high frequency content and scaled so that the reflected force falls within the range of forces sensible to a human operator.

4. Shaft/Lumen 114

Like with the embodiment of FIGS. 1–3, shaft 14 could utilize sub-shaft(s) slideable in a bore through shaft 14. If more than one sub-shaft, they could be side-by-side, or concentric (tubular). Tendons with or without sliders could also be used.

5. Method of Design

There are a variety of ways the structure of a compliant end effector could be designed and implemented. The basic functions of a grasping/cutting end effector have been shown and described herein. And, as described above, one way to implement a compliant mechanism is to build structure that effects grasping (jaws converge in a first plane) if pushed with a linear force at one location and effects scissors cutting (blades on sides of jaws and jaws converge in a second plane) if pushed at a different location (or pulled from the same location). Such a structure could be designed through trial and error or empirical methods.

Optimization of such structure could be accomplished through a variety of methods or through using any of a variety of design tools, including software programming that allows the functions to be entered, along with other basic design constraints or parameters, and the program would design an optimized configuration. One such method is discussed below.

a) Optimization Routine Used to Design Compliant Tools

The optimization routine is based on a topology design method for compliant mechanisms with multiple input and output requirements. Topology design refers to the design of the connectivity of the elements in the mechanism. To design a compliant mechanism that will produce a specific output displacement with a certain input force, a mechanism having minimal stiffness (i.e. maximum compliance) in the direction of the desired output is optimal. Simply using optimization to design for a structure with minimal stiffness will result in a solution that has members of zero or minimal area, i.e., the least stiff structure is one with minimum volume. This degenerate solution results from neglecting the requirement that the mechanism must have sufficient stiffness to supply the force at the output point, as well as not fracture or buckle as the motion is executed. Thus, the desired solution may be thought of as a mechanism that is both compliant enough to execute the opening and closing of the jaws of a grasper and stiff enough to grip with sufficient force, or, similarly, a device with sufficient compliance to perform the shearing motion of scissors while also supplying sufficient cutting force. The design requirement then becomes one of maximum compliance in the path of motion plus sufficient stiffness in the direction of the output force.

The analysis may be divided into two separate loading cases: case C for cutting and case G for grasping. The analyses of the two load cases essentially are identical, thus the following equations will initially only consider only case C. To generate a structure having both the necessary compliance and stiffness, both loading cases C and G will be further divided into a flexibility condition and a stiffness condition. For the flexibility condition, force $f_C$ is applied producing displacement field $u_{C1}$, and a dummy load $f_{dC}$ is applied at the output point producing virtual displacement field $v_C$. The mutual potential energy (MPE) is used as a measure of flexibility, where maximizing MPE results in a compliant solution with the deflection at the point of interest maximized in the desired direction. Note that simply designing for minimum strain energy will result in a solution with maximum stiffness where all element areas are at the upper bound, thus it is desirable to design for a compromise solution of minimum strain energy and maximum mutual potential energy. MPE is a function of the stiffness matrix $K_1$, the actual displacement $u_{C1}$ and the virtual displacement $v_C$, and it is defined as in (1):

$$MPE_C = (f_{dC})^T \cdot u_{C1} \qquad (1)$$
$$= (K_1 v_C)^T \cdot u_{C1}$$
$$= v_C^T K_1 u_{C1}$$

To analyze the stiffness condition, the same force $f_C$ is applied at the input point, but, in order to model the tool's resistance at the point where the output force is applied, the output point is now held fixed. Strain energy (SE) can be used as a measure of stiffness of the design, as is often done in structural optimization, where minimizing strain energy results in a solution with maximum resistance. Strain energy is defined as in (2), where $u_{C2}$ is the actual displacement due to $f_C$ when the output point is fixed, and $K_{C2}$ is the new stiffness matrix, which differs from $K_1$ because of the additional fixed degrees of freedom.

$$SE_C = (u_{C2})^T K_{C2} u_{C2} \qquad (2)$$

The strain energy and mutual potential energy now represent two competing design objectives and must be combined into a single objective function using a method such as a weighted sum of SE and MPE. The weighted sum approach has its difficulties because SE and MPE may differ by orders of magnitude and thus present a scaling problem. This difficulty may be eliminated by defining the objective function, F, as a ratio of MPE to SE, which results in the objective function given by (3) (note that minimizing SE is analogous to maximizing its reciprocal 1/SE).

$$F = \text{Max}\left(\frac{MPE_C}{SE_C}\right) = \text{Max}\left(\frac{v_C^T K_1 u_{C1}}{(u_{C2})^T K_{C2} u_{C2}}\right) \qquad (3)$$

Equation (3) is the objective function for optimizing load case C, and an analogous equation is used for optimizing load case G. For a single tool to perform both C and G, we combine the functions into a single objective function using a weighted sum technique as in (4):

$$F = \text{Max}\left[\alpha\left(\frac{MPE_C}{SE_C}\right) + (1-\alpha)\left(\frac{MPE_G}{SE_G}\right)\right] \qquad (4)$$
$$= \text{Max}\left[\alpha\left(\frac{v_C^T K_1 u_{C1}}{(u_{C2})^T K_{C2} u_{C2}}\right) + (1-\alpha)\left(\frac{v_G^T K_1 u_{G1}}{(u_{G2})^T K_{G2} u_{G2}}\right)\right]$$

The scalar weighting variable $\Delta$ may then be adjusted to tweak the solution or to give more weight to a particular load case. The constraint equations for the optimization problem come from the equilibrium equations for each displacement variable (5), the limits on the design variables (6), and the maximum volume constraint (7).

The solution procedure follows that of ground structure based topology optimization; hence, the procedure begins with a ground structure or dense web of elements. The elements' cross-sectional areas, $A_1$, are the optimization design variables and are assumed circular. This type of topology optimization is a special case of sizing optimization, such that the process adjusts the cross-sectional area of each element in the ground structure to obtain a solution with optimal performance. Ultimately, many of the elements' cross-sectional areas will diminish or decrease to the lower bound and the remaining elements will define the structure's topology. The formal optimization problem is now given by the objective function F in (4) and the following set of constraint equations, where $l_i$ is element length, $V^*$ is the maximum volume of material, and N is the number of design variables.

$$K_1 u_{C1} = f_C \quad K_1 u_{G1} = f_G$$
$$K_1 v_C = f_{dC} \quad K_1 v_G = f_{dG}$$
$$K_{C2} u_{C2} = f_C \quad K_{G2} u_{G2} = f_G \qquad (5)$$
$$A_{lower} \leq A \leq A_{upper} \qquad (6)$$

$$Vol = \sum_{i=1}^{N} A_i l_i \leq V^* \qquad (7)$$

A three-dimensional ground structure of frame elements is desirable as the basis for the optimization problem to allow for motions in different planes, such as multiple input and output forces and displacements that lie in orthogonal planes. The 3-D model can be set up with a ground structure of "unit cubes." In contrast to the full ground structure that connects each node to every other node, the unit cube structure consists of a mesh of 1×1×1 cubes connected at the cube faces where each node in the cube is connected to every other node in the cube. The unit cube arrangement significantly decreases the total number of elements, which decreases computation time, while still providing acceptable solutions. The sequential linear programming technique for constrained minimization, as provided by MATLAB and similar finite element analysis programs, is desirable for solving the optimization problem. Using MATLAB's linear programming function, linprog, the linear program can be solved and used to update the values of the element areas. The step size, or maximum amount by which the areas may change for each iteration, must be limited to provide a move limit on the approximation of the linearized objective function. Convergence occurs when either the change in the objective function or the change in each design variable decreases to a critical value.

The following example illustrates the optimization analysis used for designing the compliant multifunctional scissors-grasper tool. The setup for this problem is a 7×3×2 node design domain shown in FIG. 12 where the problem is symmetric about both the y=2 and z=0 planes, thus the figure shows only a fourth of the problem. In FIG. 12, $f_C$ and $f_G$=input forces, $\Delta C$ and $\Delta G$=output deflections, both relative to two unique functions (e.g. cutting and grasping). The starting point (set of initial areas) was randomly generated, the areas were bounded between 0.001 and 1 cm$^2$, the maximum step size for each element in an iteration was 10% of its previous value, and unit forces were used. The weighting factor was set to 0.5 (i.e. both cases weighted equally), and essentially the same solution was obtained for all values of the volume constraint with at least a 25% volume fraction. FIG. 12 displays the result from the MATLAB program, along with the full 7×5×3 node solution (where all four symmetric sections are displayed).

Solid modeling software, such as PTC's Pro/Engineer, can be used to generate a model that exhibits the same characteristics as the unit cube model analyzed through the MATLAB software. FIG. 13 shows a model generated by Pro/Engineer that behaves in the same manner as the unit cube model (the "full solution") of FIG. 12. As can be seen, the input forces $f_C$ and $f_G$ can be applied to the back side of the solid model shown in FIG. 13, and the opposite ends deflect by output displacements $\Delta C$ and $\Delta G$ (i.e. the two different output functions). It should be noted, however, that the solid model shown in FIG. 13 is made of solid titanium. As such, this solid model does not exhibit the characteristics that would be desirable for a MIS tool. In order to achieve the output displacements $\Delta C$ and $\Delta G$ desired, the input forces $f_C$ and $f_G$ would have to be tremendously high. This is simply not practicable for a MIS tool. Therefore, it is desirable to have a solid model that behaves like the unit cube model of FIG. 12, but does not require the high input forces, like the solid model of FIG. 13, in order to achieve the output displacements necessary for MIS.

FIG. 7 shows a second solid model generated through Pro/Engineer that behaves exactly like the models shown in FIGS. 12 and 13, but requires less input force to achieve a required output displacement. Essentially, the solid model of FIG. 13 has been elongated to create the model of FIG. 7. Elongating the model creates lever arms. These lever arms allow a smaller input force $f_C$ or $f_G$ to produce a greater output displacement $\Delta C$ and $\Delta G$. The key to understanding this is realizing that the moments necessary to create the output displacements in the solid model of FIG. 13 are generally equal to the moments created in the solid model of FIG. 7. Because the moments are the same, the input forces necessary to achieve the desired output displacements in the solid model of FIG. 7 are far less than the input forces in the solid model of FIG. 13. By laws of mechanics, the greater the lever arm (moment arm or radius), the less the input force to create the same moment and resulting output displacement.

6. Method of Use

| Function | Force |
|---|---|
| Grasping force | 0.4 lb. Closing |
| | 0.21 lb spreading (opening) |
| Handle force | 1.95 lb. Opening-cutting |
| | 0.5 lb closing-cutting |
| | 1.75 opening-grasping |
| | 1.5 lb. Closing-grasping |
| Pull-Off Force | 0.34 lb. (using red rubber tubing) |
| Cutting Force | 0.08 lb. |

The method of using tool 10B has been described above. The compliant nature of tool 10B provides the ability to obtain some mobility from deflection of the flexible member. Energy is stored in the flexible members of the compliant web. This can be advantageously utilized to effectuate the functions of the end effector, while the mechanism is designed so that of the user can select between multiple functions, if desired. FIGS. 16A and B illustrate the forces in the pushrods that can be used with the compliant end effector of tool 10B to effect tip displacement in a simulation based on the design of tool 10B. This type of use of compliant structures appear to be promising for miniaturization of MIS end effectors, because of lack of need for rigid link assembly and the potential for binding or malfunction over time when made very small. Compliant surgical instruments also tend to be easier to clean and sterilize for reposable use than traditional mechanically linked or hinged mechanisms.

E. Exemplary Embodiment Three (Non-compliant Multifunction Cutting and Grasping and Articulating)

1. Structure

FIGS. 17–22 illustrate a third exemplary embodiment according to the present invention. This tool, referred to as tool 10C to differentiate it from tools 10 and 10B, operates similarly to the fixed link mechanism tool 10 of FIGS. 1–3 with the following differences.

2. End-Effector

Tool 10C adds what will be considered a third function, namely articulation of the distal ends of both end-effector jaws. This allows the additional function of being able to articulate (in either direction from axis 50) the clamping action of the end effector for greater dexterity in clamping and dissecting. Articulation of distal tips can be done independently of the clamping action or can be selectively enabled.

Below are parameters for an example of tool 20C:

| Component | Length |
|---|---|
| Jaws (Total length, non-articulated) | 15 mm |
| Jaws opening distance at distal ends for grasping | 15 mm |
| Scissors blade length | 7 mm |
| Scissors opening distance at distal ends | 10 mm |
| Articulated end maximum offset from longitudinal axis of instrument | 90 degrees |

The design of the end effector of tool 10C is illustrated conceptually in FIGS. 17A–E. The jaws are essentially mirror images of each other. Therefore, for embodiment 10C, the top jaw in FIG. 17A will be generally indicated by reference number 60, and the bottom jaw by reference number 60'.

FIGS. 17A and B show how jaws 60 and 60' operate in a first mode; a clamping mode where the distal tips 68 and 68' of each jaw are straight. Each jaw 60 and 60' has a base section 62 or 62' pivotally mounted along axis 52 to distal end 18 of shaft 14. Base sections 62 and 62' are adapted to pivot in a plane defined by axes 50 and 52 in response to actuation, e.g. linear movement from a sub-shaft, such as will be described later. As shown in FIGS. 17A and B, this allows jaws to function as clamping members when base and moveable sections of each jaw are aligned along axis 50. By linear action of a sub-shaft or other member extending from a handle 12 to proximal ends of jaws 60 and 60', jaws 60 and 60' can be moved between closed clamping position (FIG. 17A) and opened clamping (or dissecting) position (FIG. 17B).

FIGS. 19A–C illustrate generally one way of generating clamping movement of jaws 60 and 60' with a linearly moving sub-shaft or tube (alternatively called slider 230). Each jaw 60 and 60' has a proximal end 232 that extends proximally of pivot axis 52 and includes an elongated slot 234 or 234'. The elongated slots 234 and 234' are angularly disposed relative to axis 50 and further, are in opposite directions to one another (as seen in FIGS. 19A–C).

A common pin 236 has opposite ends which extend laterally out of the distal end of slider 230 into slots 234 and 234'. When pin 236 is in the position of FIG. 19A (with pin 236 in the proximal ends of slots 234 and 234'), the distal ends of base sections 62 and 62' of jaws 60 and 60' would be pulled into alignment with axis 50. This would close jaws 60 and 60' (see FIG. 19A). When slider 230 moves to push pin 236 to the distal ends of slots 234 and 234', jaws 60 and 60' would open (FIG. 19B).

But further, like the moveable section 68 described with respect to tool 10 in FIGS. 1–3, both jaws 60 and 60' have a moveable section, 68 and 68' respectively, that can pivot around a pivot pin 70 or 70' (defining pivot axes 54 and 54'). The structure of these jaws 60 and 60' is such, however, that moveable sections 68 and 68' can pivot in both directions relative to axis 50 (on either side of the same). The basic principle of articulation of the tips 68 of the jaw is shown by the diagrams of FIGS. 18A and B. The two parts of the jaw (base section 62 and moveable section 68) are connected by a simple pin joint located on the instrument's centerline. FIG. 18C illustrates exemplary dimensions for the combination 62 and 68. Therefore, independent of the opening of jaws 60 and 60' as shown in FIGS. 17D and E and FIG. 19C, sections 68 and 68' could be articulated away from alignment with axis 50. As illustrated in FIGS. 17D and E and FIG. 19C, they could form an articulated clamp on either side of axis 50, over a range of off-axis angles.

This articulation of tips of the jaws 60 and 60' is another functional mode for a MIS tool. Slider 230 could be operated to close or open jaws 60 and 60' with the moveable sections articulated together in either direction to increase the flexibility and versatility of clamping action of tool 10C. FIG. 18C provides an example of additional dimensional and functional parameters for one design of articulatable sections 68 and 68'.

The articulation or rotation of the tips of the jaws may be accomplished in various ways. Two examples are mechanical actuation, or by an electromechanical interface. Others are possible. FIGS. 20A–C illustrate the general principle of one example of a mechanical actuation of the articulation function.

Attached to the tip are two tendon lines, 250A and 250B, that extend down the long axis of the instrument. In a normal or reference position (FIG. 20A), tip 68 is extended straight from base section 62 (distally along axis 50). Appropriate tension on both lines 250A and B would essentially hold or lock tip 68 in that position. In the orientation shown in FIGS. 20A–C, pulling on line 250A (and releasing tension on line 250B) will pivot the tip 68 to the left around pivot pin 70 (or axis 54) (see FIG. 20C). By pulling on line 250B (and releasing tension on line 250A), the tip will pivot to the right (see FIG. 20B). Thus, be this relatively simple method, control over articulation of the tip 60 or 60' of each jaw 60 and 60', in either direction, can be actuated by linear forces (e.g. from handle 12 or otherwise).

It is to be understood that several discrete intermediate angles could be achieved for the tip articulation. To achieve locking in intermediate pivot positions, a ratchet-type mechanism can be used. In a prototype embodiment, a standard socket wrench was used. The two tendons were attached on either side of the socket wrench such that the two connection points and the pivot point of the wrench are in line. When the wrench was turned to one side it simultaneously released tension of one line while applying tension to the other. This resulted in required force to pivot the tip being supplied, while still maintaining tension in both tendons. In practice, such an optional locking mechanism would be integrated into the device.

FIG. 20D illustrates in more detail how the distal ends of the tendon lines could be attached to a tip 68. Steel cables 250A and 250B could be soldered or otherwise attached (see points 251 and 253 respectively) to opposite sides of the distal end of a moveable section 68 of a jaw 60. Cables 250A and 250B could extend proximally back from end effector 20, through shaft 14, to handle 12. As illustrated in FIGS. 20A–D, cables 250A and 250B act as tendon lines. By pulling on line 250B, tip 68 will move to the right from the viewpoint of FIG. 20B. Pulling on line 250A will move tip 68 to the left (FIG. 20C). If both lines 250A and 250B are maintained at relatively equal lengths, and in tension, tip 68 will align with axis 50.

The same structure could be used with the other jaw, 60', such that each jaw 60 and 60' would have two cables, 250A and B, and 250A' and 250B' respectively, that extend back through shaft 14 to an actuator mechanism. FIG. 20E shows that instead of having two cable ends and two solder points per tip 68, a single cable could simply be formed in a U-shape at its middle and soldered at a single point 251B, and with opposite free ends extended to handle 12, and connected to appropriate concentric tubes. Thus, by suitable user controls (preferably in or around handle 12), the articulation of the distal tip 68 of both jaws 30 and 60 can be controlled.

By appropriate control and actuating mechanisms, the user could close jaws 60 and 60' together (as in FIG. 17A), and by concurrently pulling cable 250A of one jaw 60 or 60', and cable 250B of the other jaw 60' or 60, tips 68 and 68' would articulate in opposite angular directions (as in FIG. 17C). Reversing the process, i.e. pulling cable 250B of jaw 60 and cable 250A of jaw 60', would move tips 68 and 68' back to the position of FIG. 17A. Thus, scissors action can be accomplished.

Alternatively, to simplify a scissors function, one tip 68 or 68' could be maintained in a straight position aligned with axis 50, and the other tip 68' or 68 articulated angularly outward, by pulling on the appropriate cable 250A or 250A', and then bringing the tip back by pulling the other cable 250B or 250B'.

3. Handle

Manually actuated operation of the grasp (straight ends) mode, grasp (articulated ends) mode, or cutting mode could be accomplished by various ways. The linear push rod actuation of grasping movement for jaws 60 and 60' could be as shown and described with respect to FIGS. 19A–C, the common pin in slots arrangement. Rotational motion from handle 14 could be translated to linear motion in a number of ways, including ways previously discussed.

Articulation of tips left or right, and the cutting action could be actuated by appropriate linkage to convert rotational motion of handle 24 to pulling forces on any of the four cables or tendon lines 250A, 250B, 250A' or 250B', either alone or in combination. Additionally, a variety of ways exist for holding a tendon line in tension when a companion tendon line is being pulled.

One specific example of a system for actuating the three functions discussed above is illustrated with reference to FIGS. 21A–C and 22A–E, which illustrate a control and manual actuation mechanism to provide both clamping action according to linear movement of a push rod or slider 230 such as shown in FIGS. 19A–B, articulation of tips 68 and 68' for articulated clamping as shown in FIG. 19C by manipulation of cables attached to tips 68, and scissors action by manipulation of cables attached to one tip 68 or 68'.

As described, a notable feature of mechanism 10C is the combination of cutting, grasping and articulating into a single multi-functional instrument. The end-effector 20 shown in FIGS. 17–22 is comprised of an upper jaw 60 and lower jaw 60', each having a front or tip section 68 or 68' and rear section 62 or 62'. The front and rear sections are connected with a pin joint (along axis 52) to allow for rotation in the orthogonal plane to the grasping motion. The front and rear sections together form 15 mm grasping jaws, while the front 7 mm section 68 or 68' alone can be articulated to introduce articulated grasping or cutting features to the device. The grasping motion is operated by a push rod and pin in slot mechanism connected in the rear of the end-effector jaws as shown in FIGS. 19A–C. The cutting and articulation motions are operated using four steel cables (250A and B, 252A and B) soldered to the front portions of the end-effector jaws (two for each jaw 60/60').

The handle 12 also contains some notable mechanisms. As further described below, the four cables from the end-effector connect to the front end of four concentric tubes 350A and B, and 352A and B, placed around the grasping push rod or slider 230. The top notch of vertical fork(s) of sliding links mates with the disk at the rear of each tube and pull or free the cable(s) or push rod required for each function to operate. The concentric tubes were designed to allow the end-effector shaft to rotate freely without twisting the cables around the shaft itself. This type of connection provides a mechanical coupling between the rotational motion of the shaft and the linear motion of the sliding links to actuate the cables and push rod at any angular position of the end-effector.

More specifically, handle 12 of FIG. 21 includes the following primary parts.

A sub-shaft (or push rod or slider) 230 that is rotatably supported in hollow shaft 14 between a proximal end near the rear of handle housing 12 and a distal end that is connected to jaws 60 and 60' in the manner of FIGS. 19A–C. Sub-shaft 230 extends out of handle 12 and through shaft 14 to end effector 20. Like the configuration of FIGS. 19A–C, a transverse pin 236 in the distal end of sub-shaft 230 cooperates with slots 234 and 234' in the proximal ends of jaws 60 and 60' so that linear movement of sub-shaft 230 causes opening and closing of jaws 60 and 60' in clamping mode. A wheel control 28, fixedly mounted on sub-shaft 230, allows the surgeon to rotate end effector 20 three hundred sixty degrees relative to axis 50.

Four tubes 350A, 350B, 352A and 352B are concentrically mounted around sub-shaft 230 and are slideable along sub-shaft 230. At the proximal end of each tube 350A, 350B, 352A and 352B is fixed a disc 341, 343, 345, and 347, respectively, each of which is rigid to and moves with its respective tube. At the distal end of each tube 350A, 350B, 352A and 352B is a flange 342, 344, 346, and 348 respectively, which is rigid to and moves with its respective tube. Cables 250A, 250B, 252A and 252B, are fixed (e.g. by soldering or clamped by a screw) to flanges 342, 344, 346, and 348 respectively. Flanges 342, 344, 346, and 348 are preferably rotationally offset or radially offset relative to centerline 50 so that there is open space between each cables exit from the proximal end of shaft 14 to its respective flange.

As can be appreciated, this arrangement provides each cable a terminating structure in handle 12 that is moveable only linearly and generally parallel to axis 50. Therefore, any of the four cables can be pulled by sliding the appropriate concentric tube along sub-shaft 230. Thus, articulation control, in both directions, for either tip 68 or 68' is available at handle, and articulate can be effected through linear motion.

Moreover, each tube is independently slideable. Therefore, any combination of articulation of tips 68 and/or 68' is possible through the movement of any one or more of the tubes, alone or in combination. Still further, wheel control 26 allows rotation of the orientation of jaws 60 and 60', and thus their tips 68 and 68' at the end effector over a complete 360 degrees range, without any tangling of the cables because the tubes can freely move along with sub-shaft when rotated.

Actuation of a grasping action for jaws 60 and 60' can be effectuated by linear movement of sub-shaft 230 along axis 50. One way is by moving control wheel 26 along axis 50, or otherwise applying forces that cause sub-shaft 230 to move along axis 50. This action could be accomplished by a wide variety of methods, including those previously discussed herein, both manual and motor or actuator driven.

Control of actuation of tips 68 and/or 68' can similarly be achieved through a wide variety of methods, manual or automated. The specifics and complexity can be left to the designer based on considerations deemed relevant.

One example of a system for providing actuation of grasping (straight ends), grasping (articulated end(s)), and cutting, is illustrated at FIGS. 21A–22E, with particular reference to FIGS. 21A–C.

Handle 22 is fixed to the handle housing 12. Handle 24 is rotatably mounted to housing 12, and rotates towards handle 22 around pivot axis 25. Handle 24 includes a key slot 410 which receives and retains the key head 412 at one end of handle link 402. The other end 414 of link 402 is T-shaped.

A set of three what will be called sliding links 370, 380 and 390 fit side by side in cage 406.

A combination articulation and cut/grasp switch 400 has opposite heads 420 and 422 joined by a reduced size intermediate section 424. Two tongues 426, 428 extend from the top side of intermediate section 424. Tongue 426 is the width of a single sliding links and tongue 428 is the width of 2 sliding links. There is a gap between these 2 tongues the width of on sliding link.

The geometry of each sliding link 360, 370, and 380 is illustrated in FIGS. 21B and C.

Shortest link 360 includes a vertical fork 361 with a slot 362 sized to slideable receive the thickness of control wheel 26, a proximal arm 363 with a T-slot 364 sized to sliceable receive T-head 414 of handle link 402; and a distal arm 365 including a cut-out 366 sized to sliceable receive tongue 426 of switch 400. The length of link 360 between ends 363 and 365 is much shorter than the length of cage 406, so that link 360 can slide independently of links 370 and 380, and within cage 406.

Middle sliding link 370 is similar to link 360 relative to its vertical fork and slot 371/372, its proximal arm and t-slot 373/374, and a middle section with bottom cut-out 375/376. The main differences are that fork 371 is farther distally than fork 361, and a distal leg 377 extends farther distally and includes a second fork 378 having a slot 379. Fork 378 is also pivotally connected at pivot 393 to arm 377, and pivots around point 392 in a parallel plane to the plane defined by fork 371 arm 373 and arm 377. Furthermore, fork 378 is pivotally pinned to handle housing 12 at its middle (see pivot pin hole 393). Thus, fork 378 can not move as a whole with sliding link 370, but pivots when sliding link 370 slides.

Sliding link 380 is similar to link 370 relative to its vertical fork and slot 381/382, its proximal arm and t-slot 383/384, and a middle section with bottom cut-out 385/386, and a distal leg 387 extending distally and including a second fork 388 having a slot 378 with fork 388 being pivotally connected at pivot 394; and fork 388 is pivotally pinned at 395 to housing 12, like fork 378. The main differences are that fork 381 is farther distally than fork 371. Fork 388 is spaced the same distance from fork 381 as fork 378 is from fork 271.

When assembled, intermediate portion 424 of switch 400 is positioned laterally in cage 406 in alignment with the longitudinal slots along the sides of cage 406, with opposite heads 420 and 422 of switch 400 positioned outside on opposite sides of cage 406. Therefore, any movement of switch 406 lateral to axis 50 will cause following movement of cage 406. Sliding links 360, 370, and 380 are placed side-by side through the open top of cage 406 in the order shown in FIG. 21B, and with cut-outs 366, 376, and 386 aligned with intermediate section 424 of switch 400. In such position, each proximal end 363, 373, 383 of links 360, 370, and 380 are laterally aligned at the rear end of cage 406.

End guide 405 is installed in the rear end of cage 406 as shown in FIG. 21. It has an opening through which can pass T-head 414 of link 412, but serves to support and guide the middle of link 402, which would extend generally straight back to its connection to slot 410 in handle 24. End guide does not allow lateral movement of T-head 414 relative to cage 406. Cover 404 would be installed over cage 406, which has a longitudinal slot through which forks 361, 371, 379, 381, and 388 extend. Also, cover would be fixed against movement by connection to the body of handle 12.

This sub-assembly of cage, sliding links, and switch is supported inside handle housing 12 in a manner that allow it to move laterally somewhat, but not along its longitudinal axis, which would be parallel to sub-shaft 230 and axis 50 of tool 10C. But further, sliding links 360, 370, and 380 can slide longitudinally within cage 406; link 360 substantially, link 370 less, and link 380 less, as their opposite ends limit such travel.

Still further, switch 400 can slide transversely of the longitudinal axis of cage 406, but when a tongue 426, 428, or 230 is aligned with a cut-out 366, 376, or 386, the respective sliding link(s) can not slide longitudinally if switch 400 is held against longitudinal movement, or the respective sliding link(s) move is correspondence with longitudinal movement of switch 400. Conversely, if a tongue is not aligned with such a cut-out, that sliding link can slide longitudinally relative to switch 400. The respective link(s) simply slide over the middle section of switch 400 as no tongue impedes such movement.

FIGS. 21A and C show the relationship of the sliding links 360, 370, and 380 with concentric tubes 350A, 350B, 352A, and 352B when tool 10C is assembled. When assembled, notches 362, 372, 382, 379 and 389 are positioned to receive the edge of control wheel 26, disc 345, disc 343, disc 347, and disc 341, respectively, allowing rotation but not longitudinal movement of the same, unless the sliding link of the respective notch is moved along its allowed path of travel. This arrangement puts control over grasping action of the tool jaws by control of movement of sliding link 360, because such movement controls longitudinal movement of sub-shaft 320. It puts control over articulation of tips 68 and 68' by control of movement of sliding links 370 and/or 380 because such movement controls pulling of cables 350A and B and 352A and B, which control left and right concurrently articulation of tips 68 and 68'. It puts control over cutting action by control of movement of sliding link 370, because such movement controls pulling of cables 350A and B which controls articulation movement of one tip 68 away from and back to fixed tip 68' to effectuate scissors action.

The logical organization of this multi-functional tool 10C can be shown with reference to the state diagrams of FIGS. 22A–E.

Straight end grasping mode: Handle 24 is moved to its end limit closed to fixed handle 22. Switch 400 is moved laterally so that sliding link 370 is positioned in the gap between tongues 426 and 428 and cut-outs 376 and 386 are aligned with tongue 428. This lateral motion of switch 440 also pulls end 414 of link 402 into t-slot 364 of link 370 therefore providing a linkage from link 370 through link 402 to 410 the moving handle. Thus, tips 68 and 68' would be straight (aligned along axis 50). Switch 400 is pulled all the way out. The geometries are configured so that this action will pull cage 406, and thus all of links 360, 370, and 380, to a position that aligns T-head 414 with T-slot 364 in link 360. This also has control wheel 26 to its rearmost position, and thus, likewise, sub-shaft 230. As indicated in FIG. 22A, tips 68/68' would therefore be straight, aligned and closed (gripping action—jaws closed).

Thus, switch 400 can slide back and forth along slot 410 which lengthens and shortens the cables, but the tongues in the cut-outs make both sliding links 370 and 380 slide together, the same direction and the same distance. This therefore causes any articulation of tips 68 and 68' to be concurrent and in the same direction. Articulation can be either to the left or right, and over a range from straight to maximum angle. But further, since link 360 is linked to handle 24, jaws 60 and 60' can be opened and closed, even when tips 68/68' are articulated, by movement of handle 24. See FIG. 22B.

Compare then the scissors mode: Switch 400 is moved front or back to an intermediate position between fully forward and fully backward. Cage 406 is moved laterally by pushing switch 400 laterally such that T-head 414 is now in T-slot 374 of sliding link 370. During cutting mode, tongue 426 is located in slot 366 of link 370, link 380 is located in the gap between tongues 426 and 428, and tongue 428 is located in slots 376 and 386 of links 380 and 390, and head 420 of switch 400 is captured against longitudinal movement in slot 440; effectively locking links 360 and 380 from sliding or moving (and thus locking out grasping or articulation of tip 68'). Therefore, rotational movement of handle 24 would translate into linear movement of link 402, which would slide sliding link 370, which slides concentric tubes 352A and 352B, which are connected to cables 252A and 252B (both sides of tip 68'). Forward movement of handle 24 towards handle 22, causes rearward movement of link 402 and sliding link 370, causes rearward sliding of tubes 352A and due to the reversing pivoting motion of 378, forward motion of 352B is produced Sliding links 360 and 380 are locked in place, so tip 68 stays in a straight position. Opposite movement of handle 24 produces an opposite action. This process can be repeated to repeat scissors action. See FIG. 22C.

The preferred feature of disallowing articulation when cutting is accomplished by the fact that a section of 400 is rigidly captured in opening 442 preventing any forward or rearward sliding motion of the articulation switch 400. On the other hand, the functionality of switch 400, in combination with the sliding links, allows articulation (if desired), during clamping action, by allowing sliding links 370 and 380 to move (in unison) while sliding link 360 is connected to handle link 402. The surgeon merely adjusts switch 400 forward/rearwardly along slot 440, and slides switch 400 one way along slot 440 for articulation of tips 68/68' in one direction relative to axis 50, and the other way for articulation the other way.

Thus, actuation of multi-function tool 10C is accomplished by manual manipulation of multi-action switch 400 and moveable handle 24. Switching of articulation/ function toggle switch 400 between 2 lateral positions sets whether tool 10C is in grasping or cutting mode. While in cutting mode, articulation is not allowed by the physically blocking of the forward/rearward motion of the articulation switch by 400's position in slot 442. Articulation is possible during grasping mode when 400 is not engaged in slot 442 and forward motion of 400 in slot 440 is allowed. Sliding 400 forward and rearward operates articulation. Pivoting handle 24 operates cutting or grasping.

4. Shaft 14

Shaft 14 can be similar or the same to those previously discussed, or some other way of translating appropriate motion to the end effector can be used.

5. Method of Use

While in grasping mode, end effector 20 can also be articulated to the left or right by sliding the articulation switch forward or backward. During cutting, the articulation feature is disabled. To avoid accidental switching between functions, the toggle switch can only be switched between cutting and grasping when the jaws of the instrument are in the closed, unarticulated position.

A prototype of tool 10C accomplished the following:

| Function | Force |
|---|---|
| Grasping force | 1.1 lb |
| Force Input at Handle | 9.0 lb |
| Pull-Off Force | 2.3 lb. (using red rubber tubing) |
| Cutting Force | 1.4 lb |

F. Options and Alternatives

It will be appreciated that the present invention can take many forms and embodiment. The included exemplary embodiments are given by way of example only, and not by way of limitation to the invention, which is solely described by the claims herein. Variations obvious to one skilled in the art will be included within the invention defined by the claims.

For example, the concepts of the invention are applicable to laparoscopy, but can also be applied to other MIS techniques and/or procedures requiring similar advantages. Examples include, but are not limited to, gynecology, urology, thoracic, arthroscopy, ENT, pediatric, neurosurgery.

Furthermore, the invention can be applicable to developing procedures. A few examples include robotic, flexible scopes, and catheter-based surgeries.

The exemplary embodiments have been described in the context of a grasper and/or cutter. Other functions are possible. Examples are dissection (moving ends outwardly against tissue instead of grasping by closing, or using the blunt end with both jaws closed to scrape or separate tissue).

Further, other adjunct functions can be added to the tool. One example is cauterization (by electrification of at least one tip end). Others include such things as irrigation, suction, or other functions, which could be delivered to the internal surgical site with the device (e.g. by attaching the distal end of an irrigation or other tube or delivery conduit to an articulatable jaw member).

In-between maximum rotation and the straight position of the articulating tips, structure could be used to allow the tool to lock into a plurality of intermediate positions. Some type of ratcheting system (operating like a ratchet wrench), might be used to accomplish this. Or there could be some infinitely variably adjustable mechanism to allow the surgeon the ability to lock the tip at any angle between end limits.

Other means of actuating the articulation and opening/closing of jaws themselves may be employed. For example, the tendon wire/ratchet mechanism discussed could be replaced with a more compact mechanism for mechanical actuation. The articulation and jaw opening/closing might also be accomplished by small electromechanical actuators controlled by the surgeon using a trigger or other input device on the tool handle.

Any of the embodiments, pin-jointed or compliant, could utilize mechanical link joint and/or compliant actuation.

What is claimed is:

1. A multifunction tool for use in minimally invasive surgery, comprising:
   (a) an elongated shaft or flexible scope adapted to be inserted into a patient's body, and having opposite first and second ends;
   (b) a control handle on the first end;
   (c) a tool head on the second end, the tool head including a pair of jaws pivotal about a first axis so as to provide a first function and pivotal about a second axis so as to provide a second function; and
(d) an actuator operatively connected to the handle and the tool head to move the jaws in response to user input at the handle, the actuator comprising a compliant mechanism which has an input interface that changes the orientation and plane of movement of the jaws in response to the location and amount of force applied to the interface.

2. The tool of claim 1 wherein the jaws each have a grasping surface and a cutting edge.

3. The tool of claim 1 wherein the actuator includes a push rod for pivoting the jaws about the first axis.

4. The tool of claim 1 wherein the actuator includes wires for pivoting the jaws about the second axis.

5. The tool of claim 1 wherein the first and second axes are perpendicular to one another.

6. The tool of claim 1 wherein the tool head is articulated such that the first and second functions are performable at various angles.

7. The tool of claim 1 wherein each jaw includes an inner end pivotal about the first axis and an outer end pivotal about the second axis.

8. The tool of claim 7 wherein the outer ends of the jaws are pivoted in opposite directions for the cutting action.

9. The tool of claim 7 wherein the second ends of the jaws are pivotal in the same direction about the second axis to provide for articulated grasping and cutting.

10. A multifunction end-effector tool for use in minimally invasive surgery, comprising:
(a) a mechanism adapted to be inserted into a patient's body, the mechanism comprising;
(b) a tool head, the tool head including a pair of jaws pivotal about a first axis so as to provide a first function and pivotal about a second axis so as to provide a second function; and
(c) an interface adapted for operative communication with a control external of the patient's body and to an actuator operatively connected to the tool head to move the jaws in response to user input from a control, the actuator comprising a compliant mechanism which has an input interface that changes the orientation and plane of movement of the jaws in response to the location and amount of force applied to the interface.

11. The tool of claim 10 wherein the jaws each have a grasping surface and a cutting edge.

12. The tool of claim 10 further comprising an actuator, wherein the actuator includes a push rod for pivoting the jaws about the first axis.

13. The tool of claim 10 wherein the actuator includes wires for pivoting the jaws about the second axis.

14. The tool of claim 10 wherein the first and second axes are perpendicular to one another.

15. The tool of claim 10 wherein the tool head is articulatable such that the first and second functions are performable at various angles.

16. The tool of claim 10 wherein each jaw includes an inner end pivotal about the first axis and an outer end pivotal about the second axis.

17. The tool of claim 10 wherein outer ends of the jaws are pivotable in opposite directions for cutting action.

18. The tool of claim 17 wherein the outer ends of the jaws are pivotable in the same direction about the second axis to provide for articulated grasping and cutting.

19. A multifunction tool for use in minimally invasive surgery, comprising:
(a) an elongated shaft or flexible scope adapted to be inserted into a patient's body, and having opposite first and second ends;
(b) a control handle on the first end;
(c) a tool head on the second end, the tool head including a pair of jaws pivotal about a first axis so as to provide a first function and pivotal about a second axis so as to provide a second function; and
(d) an actuator operatively connected to the handle and the tool head to move the jaws in response to user input at the handle, the actuator comprising a compliant mechanism including an interface that changes the orientation and plane of movement of the jaws in response to the location and amount of force applied to the interface.

20. A multifunction end-effector tool for use in minimally invasive surgery, comprising:
(a) a mechanism adapted to be inserted into a patient's body, the mechanism comprising;
(b) a tool head, the tool head including a pair of jaws pivotal about a first axis so as to provide a first function and pivotal about a second axis so as to provide a second function; and
(c) an interface adapted for operative communication with a control external of the patient's body and to an actuator operatively connected to the tool head to move the jaws in response to user input from a control, the actuator comprising a compliant mechanism that changes the orientation and plane of movement of the jaws in response to the location and amount of force applied to the interface.

21. A multifunction tool for use in minimally invasive surgery, comprising:
(a) an elongated shaft or flexible scope adapted to be inserted into a patient's body, and having opposite first and second ends;
(b) a control handle on the first end;
(c) a tool head on the second end, the tool head including a pair of jaws pivotal about a first axis so as to provide a grasping function and pivotal about a second axis so as to provide a cutting function; and
(d) an actuator operatively connected to the handle and the tool head to move the jaws in response to user input at the control handle, the actuator comprising a compliant mechanism including an interface that changes the orientation and plane of movement of the jaws in response to the location and amount of force applied to the interface.

22. A multifunction end-effector tool for use in minimally invasive surgery, comprising:
(a) a mechanism adapted to be inserted into a patient's body, the mechanism comprising;
(b) a tool head, the tool head including a pair of jaws pivotal about a first axis so as to provide a grasping function and pivotal about a second axis so as to provide a cutting function; and
(c) an interface adapted for operative communication with a control external of the patient's body and to an actuator operatively connected to the tool head to move the jaws in response to user input from a control, the actuator comprising a compliant mechanism that changes the orientation and plane of movement of the jaws in response to the location and amount of force applied to the interface.

* * * * *